(12) United States Patent
Yu

(10) Patent No.: US 9,211,249 B2
(45) Date of Patent: Dec. 15, 2015

(54) METHODS AND COMPOSITIONS FOR TRANSDERMAL DELIVERY OF CAFFEINE IN THE FORM OF SOLUTIONS OR SUSPENSIONS

(71) Applicant: Benjamin M. Yu, Plainfield, IL (US)

(72) Inventor: Benjamin M. Yu, Plainfield, IL (US)

( * ) Notice: Subject to any disclaimer, the term of this patent is extended or adjusted under 35 U.S.C. 154(b) by 72 days.

(21) Appl. No.: 14/203,325

(22) Filed: Mar. 10, 2014

(65) Prior Publication Data

US 2014/0256749 A1 Sep. 11, 2014

Related U.S. Application Data

(60) Provisional application No. 61/774,952, filed on Mar. 8, 2013, provisional application No. 61/802,341, filed on Mar. 15, 2013.

(51) Int. Cl.

| | |
|---|---|
| *A61K 31/522* | (2006.01) |
| *A61K 47/14* | (2006.01) |
| *A61K 9/00* | (2006.01) |
| *A61K 9/08* | (2006.01) |
| *A61K 9/12* | (2006.01) |

(52) U.S. Cl.
CPC ............... *A61K 9/0014* (2013.01); *A61K 9/08* (2013.01); *A61K 9/12* (2013.01); *A61K 31/522* (2013.01); *A61K 47/14* (2013.01)

(58) Field of Classification Search
CPC .......................... A61K 31/522; A61K 47/14
USPC ..................................................... 514/263.34
See application file for complete search history.

(56) References Cited

U.S. PATENT DOCUMENTS

| | | |
|---|---|---|
| 3,961,060 A | 6/1976 | Fuxe |
| 4,945,094 A | 7/1990 | Salim |
| 2003/0165585 A1 | 9/2003 | Mann |
| 2014/0057873 A1 | 2/2014 | Farber |

OTHER PUBLICATIONS

United States Patent and Trademark Office, International Search Report and Written Opinion dated Jun. 23, 2014 for PCT/US14/22157.

*Primary Examiner* — Raymond Henley, III
(74) *Attorney, Agent, or Firm* — Perkins Coie LLP; Yingli Wang

(57) ABSTRACT

One aspect of the invention relates to caffeine-containing compositions comprising caffeine and one or more esters. The caffeine-containing compositions disclosed herein can be used for effective transdermal delivery of caffeine to a subject. Another aspect of the invention relates to applications and preparations of the caffeine-containing compositions.

19 Claims, 11 Drawing Sheets

METHODS AND COMPOSITIONS FOR TRANSDERMAL DELIVERY OF CAFFEINE IN THE FORM OF SOLUTIONS OR SUSPENSIONS

PRIORITY CLAIM

This application claims priority to U.S. Provisional Application Ser. No. 61/774,952, filed Mar. 8, 2013; and U.S. Provisional Application Ser. No. 61/802,341, filed Mar. 15, 2013, which are incorporated herein by reference in their entireties, as if fully set forth herein.

BACKGROUND

Caffeine is the world's most commonly consumed psychoactive compound. Caffeine is recognized to have a wide array of physiological and pharmacological effects that include mental stimulation and wakefulness, sustainment of intellectual activity, increased cardiovascular endurance, and increased metabolic function. Therapeutically, caffeine is employed as an analgesic and a mild diuretic.

Generally, caffeine is administered orally. However, oral administration of caffeine has a number of limitations. For example, caffeine has an intensely bitter taste and is often unpalatable unless heavily masked with often-undesired sweeteners and other additives in a significant amount of fluid. Alternative methods of administration have emerged, but also have their limits.

Consequently, there exists a need for a method to deliver caffeine.

SUMMARY OF THE INVENTION

One aspect of the invention relates to a caffeine-containing composition is capable of delivering a physiologically active dose of caffeine transdermally. In certain embodiments, the caffeine-containing compositions increase the solubility of the caffeine in the composition and enhance its skin penetration rate. Caffeine dissolves very well in some organic solvents, but these solvents may damage the skin and be toxic to humans and animals. Water, ethanol, isopropanol, and other non-toxic solvents may be used for the transdermal delivery of caffeine-containing compositions, but caffeine's solubility in water and many other solvents is generally low at room temperature. In certain embodiments, with the presence of helper esters (e.g. esters of amino acids, such as L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc., and esters of other acids, such as 2-(dialkylamino)ethyl 2-(4-isobutylphenyl)propionate hydrochloride, 2-(dialkylamino)alkyl 2-acetoxybenzoate hydrochloride, etc.) and solvents, the solubility of caffeine in water at room temperature and the skin penetration rate of caffeine have been increased significantly.

Another aspect of the invention discloses methods for syntheses of the helper esters. In certain embodiments, esters can be prepared by reacting a suitable organic acid and a suitable alcohol in the presence of one or more catalysts, such as HCl, HBr, oxalyl chloride, sulfone dichloride, etc.

Another aspect of this invention discloses methods for the transdermal delivery of caffeine-containing compositions disclosed herein. In certain embodiments, a caffeine-containing composition may be administered in a fine mist or stream of liquid via a spray bottle to various locations on the skin, including the neck, upper arms, wrists, back and hip. In other embodiments the caffeine-containing composition may be administered by via a roll-on bottle, a cotton swab, or other method of transferring the composition intact from its container to the desired target region on the skin.

Another aspect of this invention discloses methods for using the caffeine-containing compositions for purposes such as, but not limited to, increasing mental stimulation, wakefulness, cardiovascular endurance, metabolic function, sustaining intellectual activity, protecting the skin from sunlight, treating Herpes simplex infections, as an analgesic and as a mild diuretic.

Another aspect of this invention discloses the apparatuses used for transdermal delivery of these caffeine-containing compositions. In certain embodiments, the apparatus is indicated for topical application of a caffeine-containing composition and is comprised of a twist-up spray applicator. In other embodiments, the apparatus is comprised of a roll-on applicator, or another suitable device for transferring the composition from a container to the desired target region on the skin.

BRIEF DESCRIPTION OF THE DRAWINGS

In the drawings, closely related figures have the same number but different alphabetic suffixes.

Figure 1A:
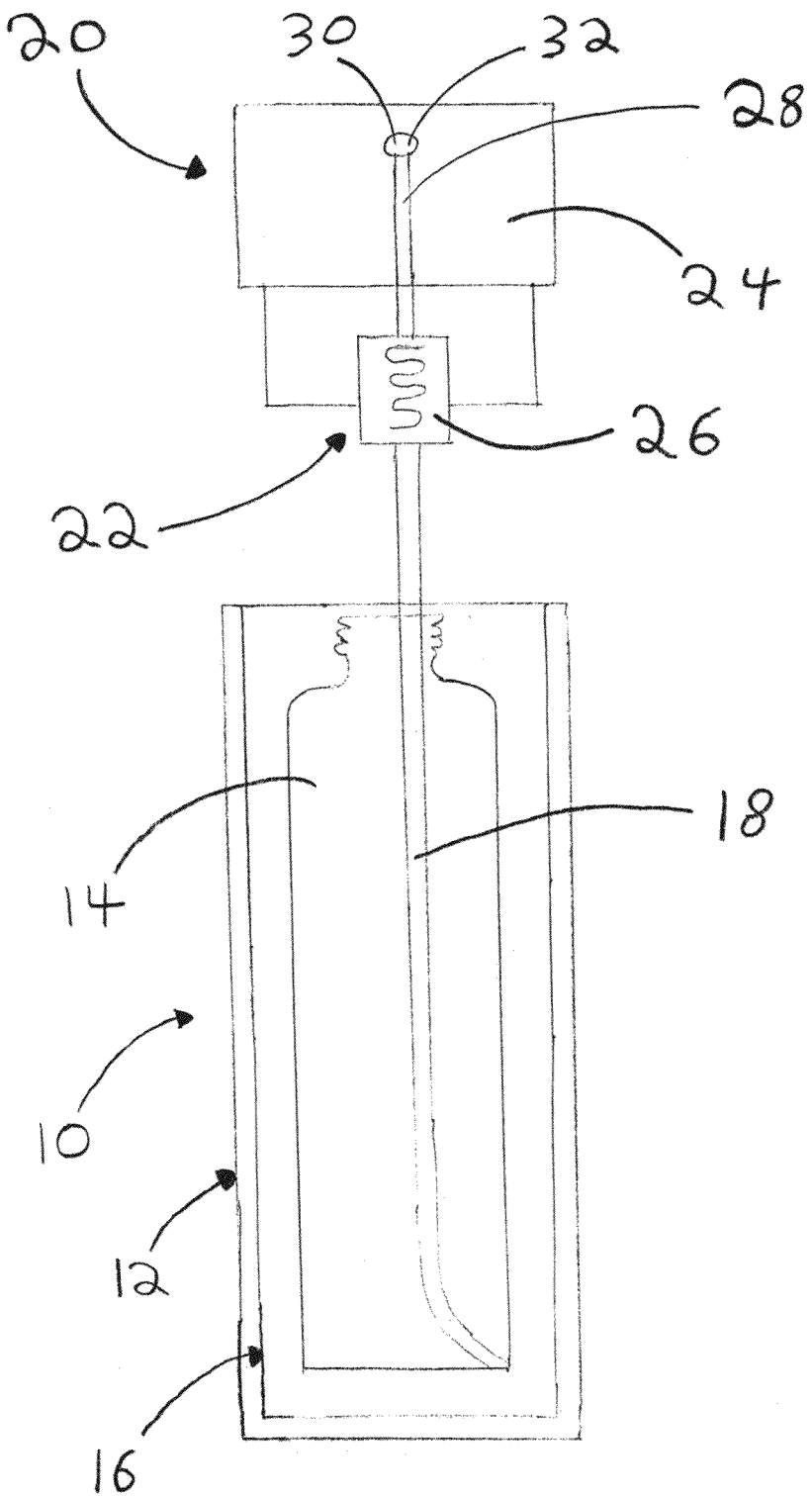
FIGS. 1A to 1B show various aspects of the exterior and interior parts of a twist-up spray applicator embodiment of the apparatus for containing and transdermally applying a caffeine-containing composition.

| DRAWINGS-REFERENCE NUMERALS | | | |
|---|---|---|---|
| 10 | twist-up spray applicator | 12 | outer enclosure |
| 14 | cylindrical bottle | 16 | inner enclosure |
| 18 | elongated tubing | 20 | cap |
| 22 | vaporizing mechanism | 24 | spray button |
| 26 | bottle check valve | 28 | hollow valve stem |
| 30 | nozzle | 32 | stem opening |
| 34 | outer casing top | 36 | outer casing middle |
| 38 | outer casing bottom | 40 | larger bottom hollow cylinder |
| 42 | larger inner encasing bottom | 44 | ridge to lock encasing top groove |

DRAWINGS-REFERENCE NUMERALS

| | | | |
|---|---|---|---|
| 46 | cut-out section | 48 | larger bottom cylinder oil |
| 50 | smaller inner encasing bottom | 52 | smaller bottom hollow cylinder |
| 54 | protruding ridges to hold bottle | 56 | smaller bottom cylinder oil |
| 58 | protrusions to fit cut-outs | 60 | top hollow cylinder |
| 62 | inner encasing top | 64 | groove to lock into encasing bottom |
| 66 | groove to fit protrusion | 68 | extended width to catch bottle cap |
| 70 | roll-on applicator | 72 | roll-on cylindrical bottle |
| 74 | plug connector | 76 | basket |
| 78 | rigid spherical ball | 80 | roll-on cap |
| 82 | ball holding groove | 84 | valve stem resisting spring |
| 86 | cylindrical seal | 88 | cylindrical seal holding spring |
| 90 | sealing circle | 92 | sealing band |
| 94 | inner bottom cap piece | 96 | outer bottom cap piece |
| 98 | screw cap grooves | 100 | inner top cap piece |
| 102 | outer top cap piece | 104 | valve stem connector |
| 106 | nozzle check valve | 108 | enclosing tube container |
| 110 | sealing band ridge | 112 | enclosing tube |

IV. DETAILED DESCRIPTION OF THE INVENTION

One or more embodiments of the invention detail caffeine-containing compositions that may be transdermally delivered through the skin. A transdermal route of delivery has numerous advantages over other routes of administration, and the particular caffeine-containing compositions disclosed here, along with the particular method and apparatus of delivery present many advantages over pre-existing methods of topical administration.

One aspect of the invention discloses the caffeine-containing compositions containing caffeine and a helper ester which may increase the solubility of the caffeine in the caffeine-containing compositions and enhance its skin penetration rate.

In certain embodiments of the invention, the helper ester, e.g. esters of amino acids, such as L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc., and esters of other acids, such as 2-(dialkylamino)ethyl 2-(4-isobutylphenyl)propionate hydrochloride, 2-(dialkylamino)alkyl 2-acetoxybenzoate hydrochloride, etc., have a one to one mole ratio to a one to ten mole ratio or ten to one mole ratio compared to caffeine in the caffeine-containing composition, and pure water is used as a solvent. It will be understood by one of ordinary skill in the art that there are more varieties of esters of amino acids and other acids than listed here that may be used.

In certain embodiments of the invention, examples of the helper esters include, without limitation:

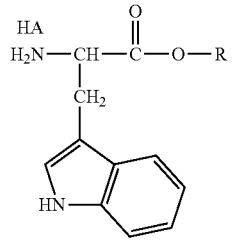

Structure 1

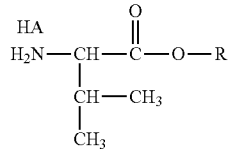

Structure 2

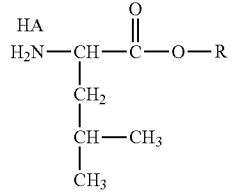

Structure 3

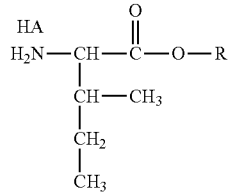

Structure 4

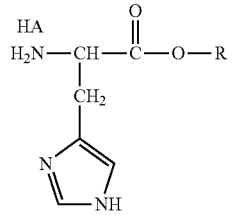

Structure 5

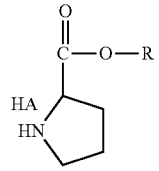

Structure 6

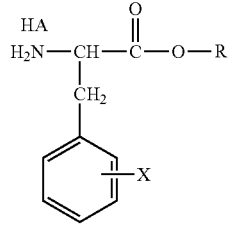

Structure 7

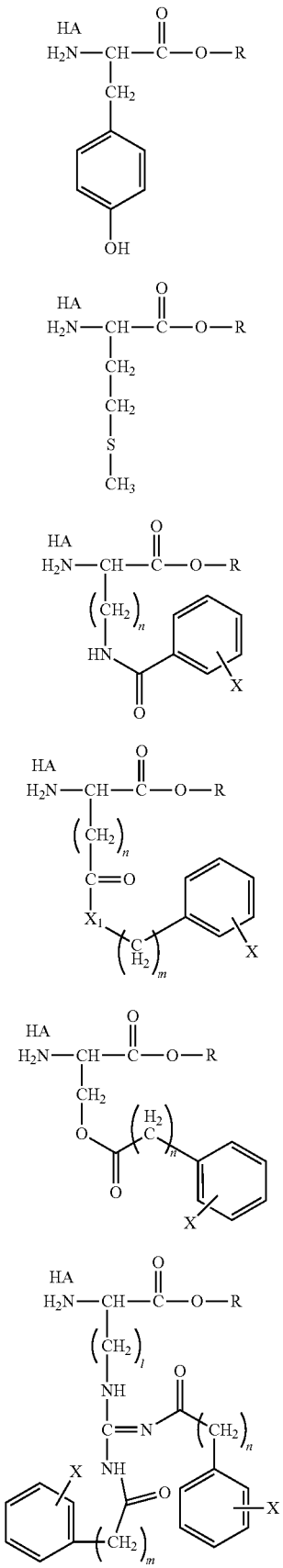

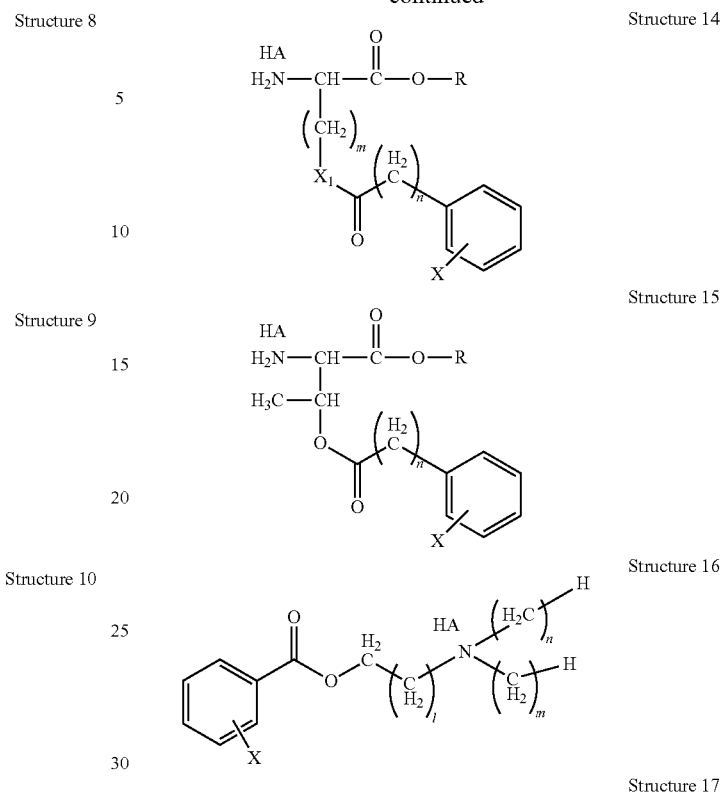

each X is independently selected from the group consisting of H, NH$_2$, NHR$_5$, OH, OCOR$_5$, Cl, Br, I, CN, R$_5$COS, R$_5$O, R$_5$OCONH, CH$_2$NHR$_8$, R$_5$SO$_2$, R$_5$SO, NH$_2$SO$_2$, and NO$_2$;

each X$_1$ is independently selected from the group consisting of O, S, NH$_2$, and NHR$_5$;

each R$_1$, R$_5$ and R is independently selected from the group consisting of H, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, NR$_1$, or any other pharmaceutically acceptable groups;

each HA is independently selected from the group consisting of HF, HCl, HBr, HI, acetic acid, citric acid, benzoic acid, lactic acid, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, and pamoic acid and any other acid that is non-toxic to humans and animals;

each l, m, and n is independently selected from the group consisting of 0, 1, 2, 3, 4, 5, 6, 7, 8, 9, and 10.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyls include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene, and dodecylene. In certain embodiments, the hydrocarbon group contains 1 to 20 carbons. In certain embodiments, the hydrocarbon group contains 1 to 10 carbons. In certain embodiments, the hydrocarbon group contains 1 to 8 carbons.

As used herein, unless specified otherwise, the term "cycloalkyl" means an alkyl that contains at least one ring and no aromatic rings. In certain embodiments, a cycloalkyl is a saturated cycloalkyl group. In certain embodiments, a cycloalkyl group comprises unsaturated bonds. Examples of cycloalkyls include, but are not limited to, cyclopropyl, cyclobutyl, cyclopentyl, cyclohexyl, cycloheptyl, cyclooctyl, cyclononyl, cyclodecyl, cycloundecyl, and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl, or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl, or heterocycloalkyl, which contains one or more halogen atoms, wherein the halogen atoms can be either the same or different. The term "halogen" means fluorine, chlorine, bromine or iodine. Examples of alkyl halides include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl, or heterocycloalkyl, which contains one or more sulfur atoms. Examples of alkylthios include, but are not limited to, —$CH_2$—SH, —$SCH_3$, —S-alkyl, -alkyl-SH, -alkyl-S-alkyl-, wherein the two alkyls can be either the same or different.

As used herein, unless specified otherwise, the term "alkylamino" means an alkyl, cycloalkyl, or heterocycloalkyl, which contains one or more nitrogen atoms. Examples of alkylaminos include, but are not limited to, —$CH_2$—NH, —$NCH_3$, —N(alkyl)-alkyl, —N-alkyl, -alkyl-$NH_2$, -alkyl-N-alkyl and -alkyl-N(alkyl)-alkyl wherein the alkyls can be either the same or different.

As used herein, unless specified otherwise, the term "alkylcarbonyl" means an alkyl, cycloalkyl, or heterocycloalkyl, which contains one or more carbonyl groups. Examples of alkylcarbonyl groups include, but are not limited to, the aldehyde group (—R'—C(O)—H), the ketone group (—R'—C(O)—R"), the carboxylic acid group (R'—COOH), the ester group (—R"—COO—R'), carboxamide, (—R'''—COO—N(R')R"), the enone group (—R''''—C(O)—C(R')=C(R")R'''), the acyl halide group (—R'—C(O)—X) and the acid anhydride group (—R"—C(O)—O—C(O)—R'), wherein R', R", R''' and R'''' are either the same or different alkyls, cycloalkyls, or heterocycloalkyls.

As used herein, unless specified otherwise, the term "perfluoroalkyl" means an alkyl, cycloalkyl, or heterocycloalkyl, which contains one or more fluoro groups, including, without limitation, perfluoromethyl, perfluoroethyl, and perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryls include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino, and benzothiazolyl.

In certain embodiments of the invention, when caffeine is coupled with esters of amino acids, such as L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc., and esters of other acids, such as 2-(dialkylamino)ethyl 2-(4-isobutylphenyl)propionate hydrochloride, 2-(dialkylamino)alkyl 2-acetoxybenzoate hydrochloride, etc., and solvents, it is possible to increase the solubility of caffeine in water at room temperature significantly. It will be understood by one of ordinary skill in the art that there are more varieties of esters of amino acids and other acids than listed here that may be used.

In certain embodiments of the invention, the solubility of caffeine in a composition is increased from the solubility of caffeine in pure water by the addition of tryptophan isopropyl ester to the composition with water as a solvent. Other esters of amino acids and other acids also increase the solubility of caffeine in water. The effects of some of these additions on the solubility of caffeine are shown in Tables 1-9 in Example 41. D-amino acid esters may increase the solubility of caffeine just as much as L-amino acid esters (Table 1). The HCl in the esters can be substituted with other acids without significantly altering caffeine's solubility in the ester composition.

In certain embodiments of the invention, the ester comprises a lipophilic portion and a primary, secondary, or tertiary amine group which forms a salt with an acid that is non-toxic to humans and animals such as, without limitation, HF, HCl, HBr, Hl, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, pamoic acid, etc.

The ability for a concentrated caffeine-containing composition to stay entirely dissolved even at cold temperatures ensures that the composition may be used in a wide variety of everyday situations.

The skin penetration rate of caffeine in caffeine-containing compositions disclosed herein may also improve significantly, as shown by improved transdermal delivery of caffeine in human (E.g. FIGS. 5A-5H, Example 41).

Figure 6:
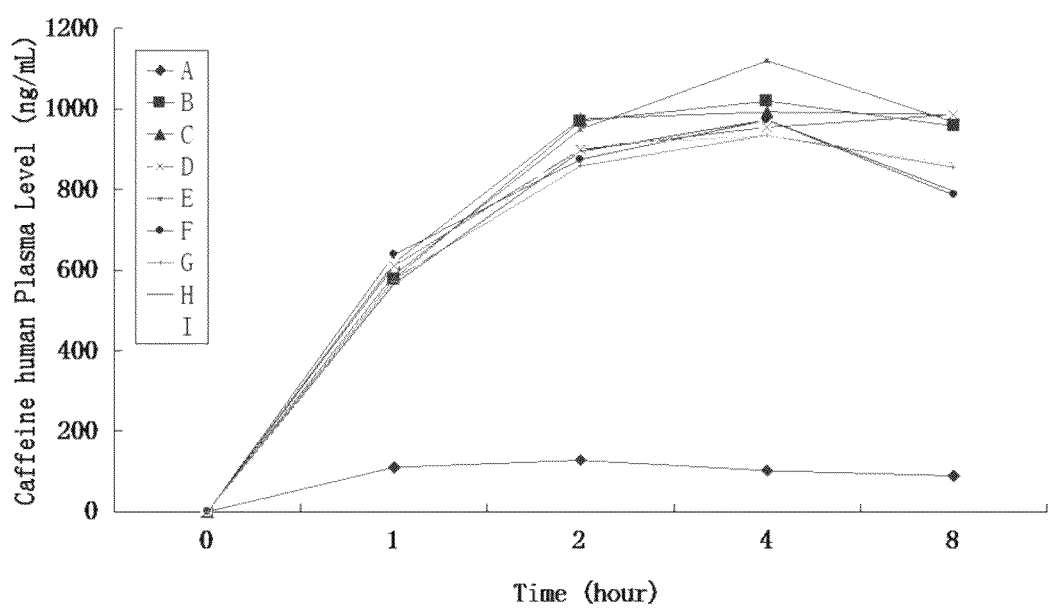
FIG. 6 shows the effects of some acid substitutions in esters on the human skin penetration rate of caffeine.

In certain embodiments of the invention, the acids (HA) in the esters of amino acids and other acids have no significant effect on the human skin penetration rate of caffeine (e.g. FIG. 6, Example 41). Thus, the HA may be changed from HCl to any acid that is non-toxic for humans and animals. Examples of suitable acids include, but are not limited to, HF, HCl, HBr, HI, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, and pamoic acid.

In certain embodiments of the invention, the caffeine-containing composition comprises caffeine, a helper ester, e.g. esters of amino acids, such as L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc., and esters of other acids, such as 2-(dialkylamino)ethyl 2-(4-isobutylphenyl)propionate hydrochloride, 2-(dialkylamino)alkyl 2-acetoxybenzoate hydrochloride, etc., and a solvent.

In certain embodiments, the caffeine-containing composition further comprises diluents, excipients, solvents, auxiliary, pH adjusting, buffering agents, and toxicity adjusting agents.

The amount of caffeine ranges from about 1 percent to about 20 percent, from about 2 percent to about 12 percent, from about 3 percent to about 10 percent, and from about 4 percent to about 7 percent of the compositions by weight. The amount of the salt of the helper ester ranges from about 1 percent to about 50 percent, from about 2 percent to about 25 percent, from about 3 percent to about 10 percent, and from about 4 percent to about 7 percent of the compositions by weight.

In certain embodiments of the invention, the caffeine-containing composition further comprises an amino acid, such as L-tryptophan, L-leucine, L-isoleucine, L-proline, L-tyrosine, L-phenylalanine, L-arginine, L-alanine, L-asparagine, L-aspartic acid, L-cysteine, L-glutamine, L-histidine, L-lysine, L-methionine, L-serine, L-threonine, L-valine, D-tryptophan, D-leucine, D-isoleucine, D-proline, D-tyrosine, D-phenylalanine, D-arginine, D-alanine, D-asparagine, D-aspartic acid, D-cysteine, D-glutamine, D-histidine, D-lysine, D-methionine, D-serine, D-threonine, D-valine, glycine, etc. The amino acid may be more beneficial to the skin, as certain amino acids are nutritionally valuable to skin and some amino acids, such as histidine, cysteine, and tyrosine are anti-oxidants that may protect the skin from oxidative damage. It will be understood by one of ordinary skill in the art that there are more amino acids than listed here that may be used. The amount of amino acids ranges from about 0.001 percent to about 50 percent, from about 0.01 percent to about 20 percent, from about 0.1 percent to about 10 percent, and from about 0.1 percent to about 2 percent of the compositions by weight.

In certain embodiments of the invention, the caffeine-containing composition further comprises water as the solvent. Generally, the amount of water ranges from about 1 percent to about 99 percent, from about 50 percent to about 95 percent, from about 70 percent to about 90 percent, and from about 75 percent to about 88 percent of the compositions by weight.

In certain embodiments of the invention, the compositions further comprises alcohols, such as ethanol, propanol, isopropanol, butanol, etc., as a solvent or co-solvent in addition to water. It will be understood by one of ordinary skill in the art that there are more alcohols than listed here that may be used. The use of alcohols as a solvent increases the evaporation rate of the composition, consequently decreasing the amount of time the composition is noticeably wet on the skin. Generally, the amount of alcohols ranges from about 1 percent to about 99 percent, from about 5 percent to about 75 percent, from about 10 percent to about 50 percent, and from about 10 percent to about 25 percent of the compositions by weight.

In certain embodiments of the invention, the compositions may also include menthol, which further aids the efficacy of caffeine's skin penetration by functioning as a vasodilator and reducing skin barrier function. In certain embodiments, alcohol, acetone, dimethyl sulfoxide (DMSO), and salts of the helper esters disclosed in this invention may be used to increase the solubility of menthol. The use of menthol may have the additional benefit of eliciting a cooling sensation when applied, which is helpful in providing direct feedback to the user that the composition has been properly administered to the desired region of skin. Generally, the amount of menthol ranges from about 0.01 percent to about 20 percent, from about 0.1 percent to about 10 percent, from about 1 percent to about 5 percent, and from about 1 percent to about 3 percent of the compositions by weight.

In certain embodiments of the invention, the compositions may also contain adjuvants such as preservatives, wetting agents, emulsifying agents and dispersing agents. Prevention of the action of microorganisms may be ensured by the inclusion of various antibacterial and antifungal agents, such as, without limitation, paraben, chlorobutanol, phenol sorbic acid, etc. It will be understood by one of ordinary skill in the art that there are more varieties of antibacterial and antifungal agents than listed here that may be used.

In certain embodiments of the invention, the compositions may include the use of glycerin as a solvent in addition to water and/or alcohol.

In certain embodiments of the invention, the compositions may include the use of dimethyl sulfoxide (DMSO) as a solvent in addition to water and/or alcohol. Generally, the amount of DMSO ranges from about 1 percent to about 80 percent, from about 5 percent to about 70 percent, from about 10 percent to about 50 percent, and from about 20 percent to about 30 percent of the compositions by weight.

Another aspect of the invention discloses the methods for preparing the caffeine-containing compositions disclosed herein.

Another aspect of the invention discloses the methods for syntheses of the esters present in certain embodiments of the invention. In certain embodiments, esters are prepared according to organic synthesis by reacting a suitable organic acid and a suitable alcohol in the presence of one or more catalysts, such as HCl, HBr, oxalyl chloride, sulfone dichloride, etc. It will be understood by one of ordinary skill in the art that there are more catalysts than listed here that may be used. Examples of specific ester preparations of one or more embodiments are disclosed below in the Examples.

Another aspect of this invention discloses uses of the compositions disclosed herein for purposes including, but not limited to, increasing mental stimulation, wakefulness, cardiovascular endurance, and metabolic function, sustaining intellectual activity, protecting the skin from sunlight and for treating Herpes simplex virus infections. In certain embodiments, the compositions can also be used as an analgesic and a mild diuretic.

Another aspect of the invention discloses methods for the transdermal delivery of these caffeine-containing compositions. Examples of particular administration apparatuses used to administer a caffeine-containing composition to a skin in certain embodiments are disclosed below, but the invention is not limited to these methods and may use any method available to administer a caffeine-containing composition to the skin.

In certain embodiments of the invention, a caffeine-containing composition is administered via a fine mist or stream of liquid dispensed via a spray bottle to various locations on the skin, such as the neck, upper back, wrists, and hip. It will be understood by one of ordinary skill in the art that these body parts are listed due to their proximity to the bloodstream, accessibility, and relatively reduced fat accumulation, among other factors. This method of transdermal delivery of a caffeine-containing composition presents multiple advantages over other topical caffeine products. The first is in the speed and ease of use.

The ability for a caffeine-containing composition spray to be inconspicuous and not visible to others also presents advantages over other topical application methods. This allows the composition to be applied in the most desirable locations physiologically speaking, such as the neck, where it is closest to blood circulation in the brain.

In certain embodiments of the invention, a caffeine-containing composition is administered via a roll-on bottle. This method of administration allows for application of the composition to a more exact region of the skin, and may be preferable for some to the spray. In certain embodiments an apparatus containing a plastic, glass, or metal roll-on ball head is employed to dispense a caffeine-containing composition to the skin by means of direct contact of the roll-on head, which is covered with a film of the caffeine-containing composition as it cycles between the reservoir of the bottle apparatus containing the caffeine-containing composition and contact with the skin. Consequently the roll-on head alternates between being in contact with the caffeine-containing composition and thereby developing a film of the caffeine-containing composition on its surface and being in contact with the skin and thereby imparting the caffeine-containing composition to the skin. This method of administration is described in further detail below.

In certain embodiments of the invention, a caffeine-containing composition is administered by employing a cotton swab to administer the caffeine-containing composition. For some, this may be the most comfortable method of application as the cotton swab may be gentler than a roll-on head yet allows for the same level of preciseness in applying the composition to a particular region of skin. A cotton swab may be dabbed in the composition, which is held in a reservoir, and then applied directly to the skin, and this procedure may be repeated as many times as necessary until the desired amount of caffeine-containing composition has been dispensed.

Several advantages are shared by transdermal methods of application. In comparison with oral ingestion, transdermal composition application eliminates aversion caused by the bitter taste of caffeine. The elimination of taste also allows the product to be delivered without unnecessary additives to make the product more palatable. There is also no need to drink a large amount of liquid along with the caffeine, hence no longer limiting one's caffeine intake to one's thirst or desire to drink. There is furthermore no risk of teeth staining and halitosis, as is often a concern with coffee, tea, and other caffeine containing oral products.

Another aspect of the invention discloses the apparatuses employed in the novel methods of delivery of the caffeine-containing compositions. One embodiment of the apparatus including a caffeine-containing composition is illustrated in FIGS. 1A (exterior view), 1B (outer enclosure) and 2 (interior view). There is shown a twist-up spray applicator 10 which in the external view shown in FIG. 1A comprises a cylindrical bottle 14, made of glass, plastic such as polypropylene, metal such as steel or aluminum, or another suitable material, for containing a caffeine-containing composition held inside an inner enclosure 16 made of plastic such as polypropylene, metal such as steel or aluminum, or another suitable material, which is in turn held in an outer enclosure 12 made of metal such as steel or aluminum, plastic such as polypropylene, or another suitable material, and a vaporizing mechanism 22 contained within and attached to a cap 20.

The cap 20 is used to seal the open top of the bottle 14 and prevent the caffeine-containing composition contained within from spilling out of the bottle 14. The vaporizing mechanism 22 contained within and attached to the cap 20 is comprised of elongated tubing 18 made of plastic such as polypropylene or another suitable material held within the bottle 14 that leads to a bottle check valve 26 comprising a ball made of glass, plastic such as polypropylene, metal such as steel, or another suitable material, which in turn leads to the cap 20. The check valve 26 is held under a hollow valve stem 28, made of plastic such as polypropylene, metal such as aluminum or steel, or another suitable material, which is connected to a stem opening 32 at the nozzle 30 of the spray button 24 part of the cap 20.

Figure 1B:
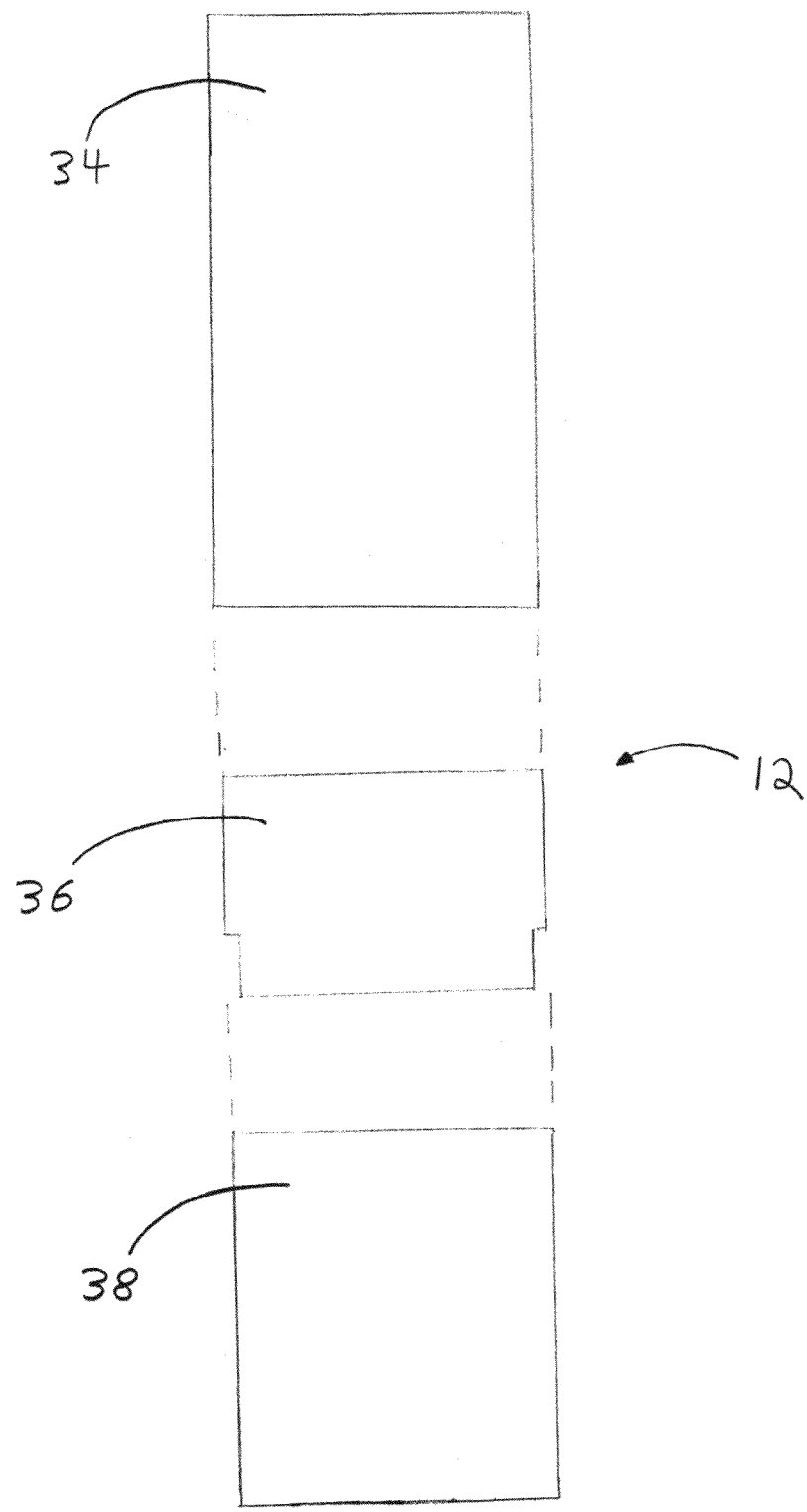

The outer enclosure 12 is further illustrated in FIG. 1B, where it can be seen divided into three parts, first the outer casing bottom 38, made of metal such as steel or aluminum, plastic such as polypropylene, or another suitable material, which contains the bottle 14 from FIG. 1A, then the outer casing middle 36, made of metal such as steel or aluminum, plastic such as polypropylene, or another suitable material, which serves to fill the space between the top and the bottom casing pieces, and finally the outer casing top 34, made of metal such as steel or aluminum, plastic such as polypropylene, or another suitable material, which serves to contain the remainder of the bottle 14 from FIG. 1A not contained by the outer casing bottom 38 and the outer casing middle 36, as well as the cap 20 from FIG. 1A.

Figure 2:
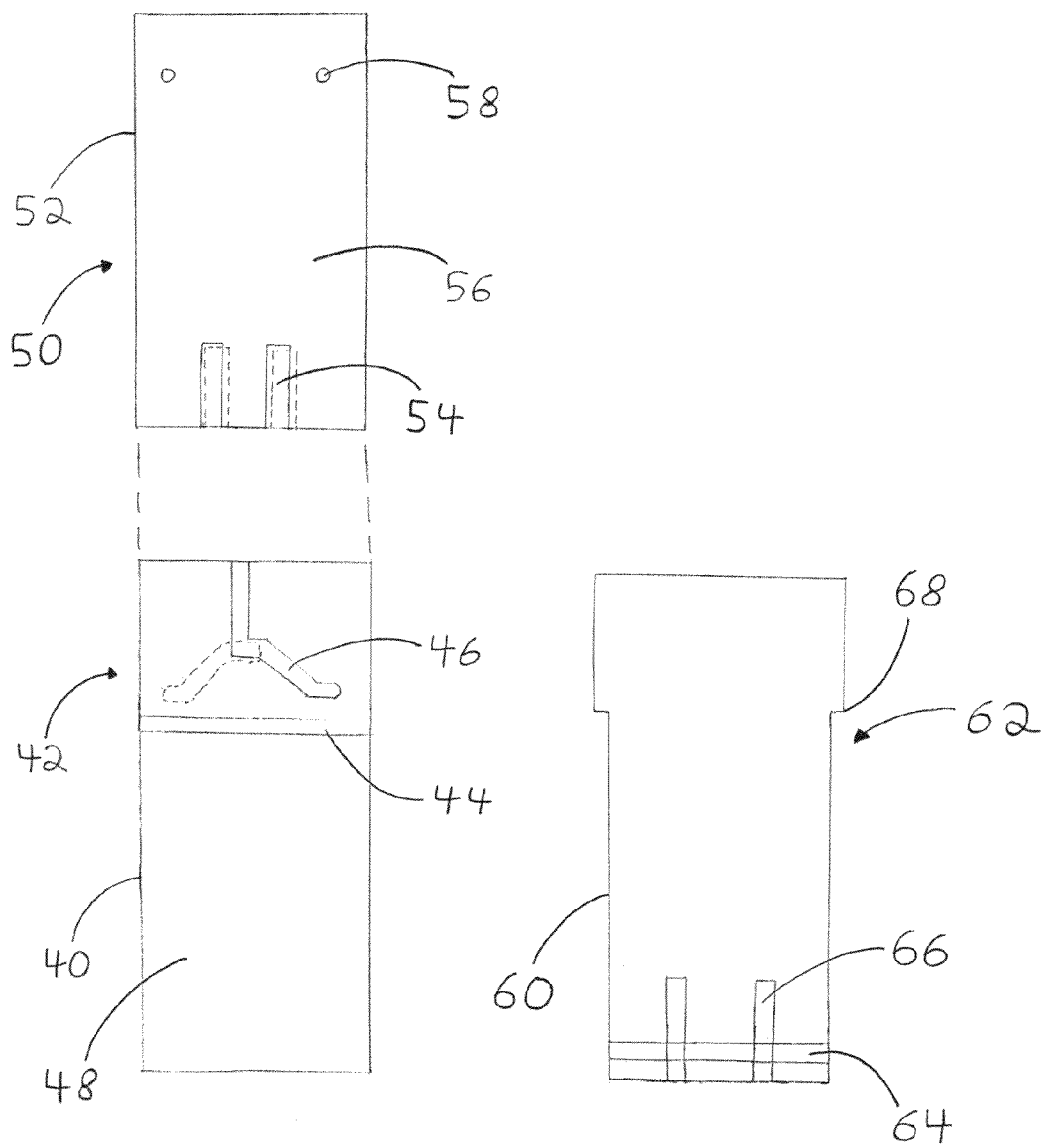
FIG. 2 shows the interior casing of the twist-up spray applicator embodiment of the apparatus for containing and transdermally applying a caffeine-containing composition that is responsible for its twist-up functionality.

The inner enclosure 16 from FIG. 1A is further illustrated in FIG. 2, where it can be seen divided into three parts as well, first the larger inner encasing bottom 42, made of plastic such as polypropylene, metal such as steel or aluminum, or another suitable material, then the smaller inner encasing bottom 50, made of plastic such as polypropylene, metal such as steel or aluminum, or another suitable material, and finally the inner encasing top 62, made of plastic such as polypropylene, metal such as steel or aluminum, or another suitable material. The larger bottom 42 piece is comprised of a larger bottom hollow cylinder 40, made of plastic such as polypropylene, metal such as steel or aluminum, or another suitable material, that has the feature of a horizontal circular ridge 44 to lock into the horizontal circular groove 64 of the encasing top 62 piece as well as two cut-out sections 46 to fit the protrusions 58 of the smaller inner encasing bottom 50. The larger hollow cylinder 40 is covered with a film of oil 48 on the outside to reduce friction while being twisted in operation by the user and coming in contact with the interior of the top hollow cylinder 60, made of plastic such as polypropylene, metal such as steel or aluminum, or another suitable material, of the inner encasing top 62 piece.

The smaller bottom 50 piece fits inside the larger bottom 42 piece and is comprised of a smaller bottom hollow cylinder 52, made of plastic such as polypropylene, metal such as steel or aluminum, or another suitable material, which features four protruding ridges 54 to hold the bottle 14 from FIG. 1A in place as well as two circular protrusions 58 to fit through the cut-out sections 46 of the larger inner bottom 42 piece and lock into the vertical protrusion holding grooves 66 of the encasing top 62 piece. The smaller hollow cylinder 52 is covered with a film of oil 56 on the outside to reduce friction while being twisted in operation by the user and coming in contact with the interior of the larger hollow cylinder 40 of the larger inner bottom 42 piece.

The encasing top 62 piece is then comprised of a top hollow cylinder 60 which features a horizontal circular groove 64 to lock the horizontal circular ridge 44 of the larger inner bottom 42 piece in place and two vertical protrusion holding grooves 40 to constrain the two protrusions 58 of the smaller inner bottom 50 piece to a narrow range of vertical movement so as to properly ensure up and down movement of the bottle 14 from FIG. 1A being manipulated by the smaller inner bottom 50 piece. There is also an extended width 68 near the top of the encasing top 62 piece to catch the metal cap 20 from FIG. 1A of the apparatus and ensure that it does not fall below the height of the encasing top 62 piece at which the extended width 68 is present.

An example of the manner of using this embodiment of the twist-up spray applicator 10 is shown in FIG. 1A. The first step is to depress the spray button 24, which then forces liquid by virtue of the closed check valve 26 through the stem opening 32 and the nozzle 30 in a very fine mist. This is accomplished by virtue of the fact that depressing the spray button 24 decreases the volume inside the vaporizing mechanism 22 from the hollow valve stem 28 to the stem opening 32, which causes excess liquid with no space inside the now decreased volume from the hollow valve stem 28 to the stem opening 32 to be ejected through the stem opening 32 and the nozzle 30. The nozzle 30 should be aimed at the region of the skin on which it is desired that the caffeine-containing composition be applied. Hence, when the caffeine-containing composition is ejected from the nozzle 30 in a fine mist by depression of the spray button 24, it will land on the desired region of the skin. The dispersion of the liquid in the form of a fine mist is accomplished by the very small size of the nozzle 30 opening, which only allows small particles of the liquid to exit, hence creating a fine mist.

Figure 4:
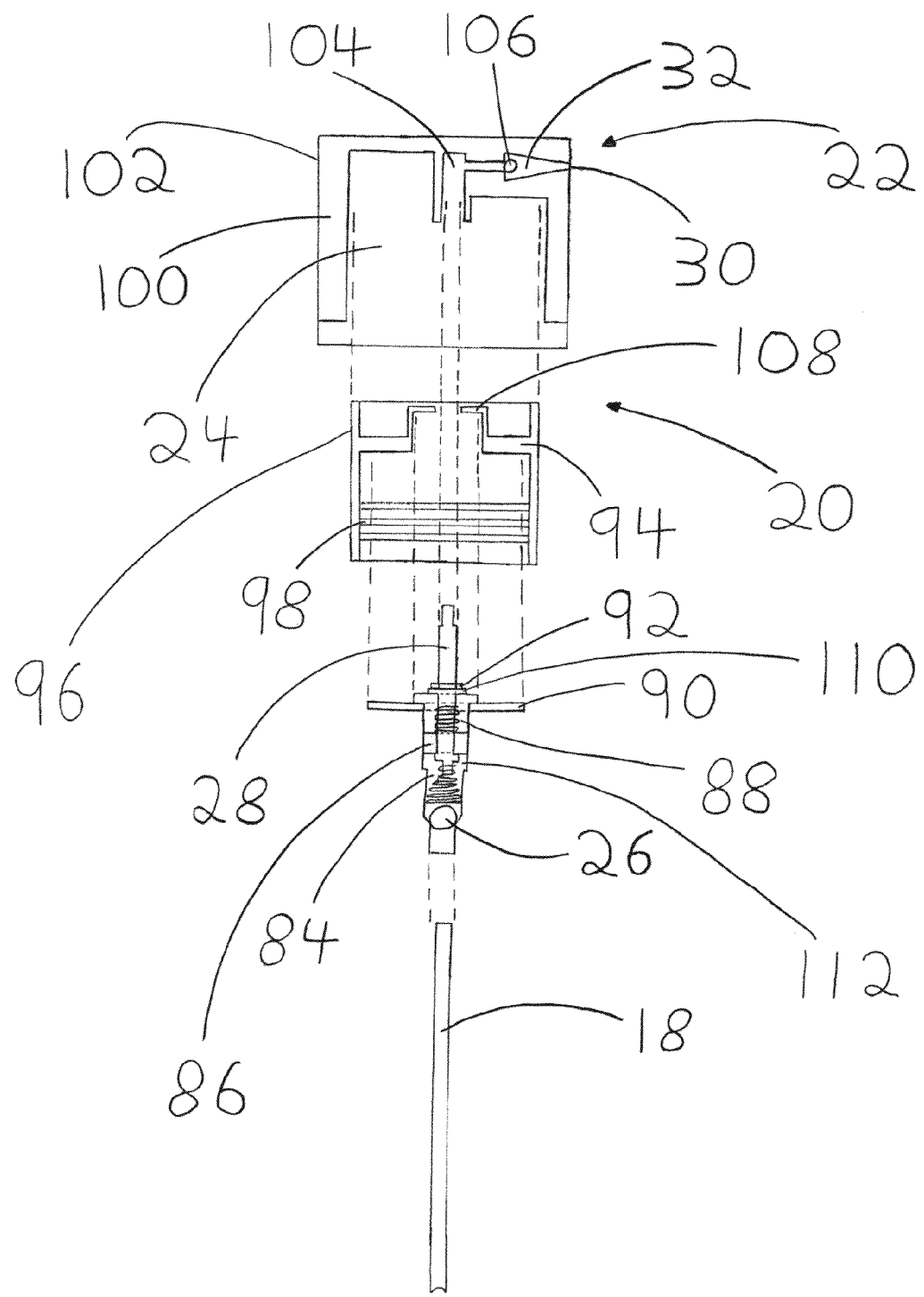
FIG. 4 shows in closer detail the vaporizing mechanism, cap, and tubing components of the twist-up spray applicator.

The collective vaporizing mechanism 22 and cap 20 structure of the twist-up spray applicator 10 from FIG. 1A is shown in FIG. 4. Here, the parts that comprise this overall vaporizing mechanism 22 and cap 20 are shown in greater detail than in FIG. 1A, and more parts are enumerated. It can be seen that the elongated tubing 18 is firmly attached to the bottom of the enclosing tube 112, which is made of plastic such as polypropylene, or another suitable material.

The enclosing tube 112 houses the bottle check valve 26 and the hollow valve stem 28. At the bottom of the valve stem 28, there is attached a valve stem resisting spring 84, made of metal such as spring steel, or another suitable material. Above the spring 84, there is the cylindrical seal 86, made of plastic such as polypropylene, or another suitable material. Above the cylindrical seal 86 is a cylindrical seal holding spring 88, made of metal such as spring steel, or another suitable material, which holds the cylindrical seal 86 in place. Above the spring 88 there is a sealing band ridge 110 and a sealing band 92, made of rubber or another suitable material, which is stretched around the sealing band ridge 110 and forms a seal across the entire width of the enclosing tube 112, just as the cylindrical seal 86 does. This prevents any liquid from the cylindrical bottle 14 from FIG. 1A from being drawn up through the enclosing tube 112, but rather only through the hollow valve stem 28.

It can be seen that the valve stem 28 passes through, and the enclosing tube 112 is contained within, the outer bottom cap piece 96, made of metal such as steel or aluminum, plastic such as polypropylene, or another suitable material, and the inner bottom cap piece 94, made of plastic such as polypropylene, metal such as steel or aluminum, or another suitable material. The inner bottom cap piece 94 is held firmly within the outer bottom cap piece 96 by virtue of having a slightly increased width towards the bottom half of the inner bottom cap piece 94, which causes the inner bottom cap piece 94 to firmly jam into the outer bottom cap piece 96 when the two are connected. The top and bottom of the outer bottom cap piece 96 are hollow, and there is an enclosing tube container 108 feature present at the inner bottom cap piece 94, which allows the valve stem 28, but not the enclosing tube 112, to pass through.

There is also a sealing circle 90, made of foam or another suitable material, which is tightly attached and glued to the enclosing tube 112 as well as the inside of the inner bottom cap piece 94 where it resides near the top of the structure, as far up as it is capable of going, which prevents the enclosing tube 112 from moving as it is held within the inner bottom cap piece 94. There are also screw cap groove lines 98 incorporated into the inner bottom cap piece 94, which allow the inner cap piece 94 to form a seal with the cylindrical bottle 14 seen in FIG. 1A, on which there are matching screw cap ridges.

The valve stem 28 connects and is firmly attached to the valve stem connector 104, which is a feature of the inner top cap piece 100, which is made of plastic such as polypropylene, metal such as steel or aluminum, or another suitable material. The inner top cap piece 100 holds snugly within it the outer bottom cap piece 96 and the inner bottom cap piece 94, and is in turn firmly attached to the outer top cap piece 102 by glue and similar dimensions. Examples of glues include, without limitation, polyurethane glue or another suitable adhesive material. As the valve stem 28 is firmly attached and snugly sealed within the valve stem connector 104, it may now be observed that there is a complete path for liquid to travel from the bottle 14 shown in FIG. 1A to the stem opening 32 and nozzle 30, and that there is no other path for liquid to travel from the bottle 14 shown in FIG. 1A but through the valve stem 28 to the stem opening 32 and nozzle 30. Within the tube leading from the valve stem connector 104 to the stem opening 32, there is present a nozzle check valve 106, which when in place fully seals the tube leading to the valve stem connector 104 and the valve stem 28, and consequently prevents air outside the vaporizing mechanism 22 from entering through the nozzle 30 and the stem opening 32 and passing through to the valve stem connector 104 and the valve stem 28.

The vaporizing mechanism 22, as shown in FIG. 4, functions to draw liquid from the bottle 14 seen in FIG. 1A, and direct it through the valve stem 28 to the stem opening 32 and nozzle 30, where it is sprayed in a fine mist to the desired target region on the skin. This is made possible by the presence of the bottle check valve 26 and the nozzle check valve 106. First, the entirety of the elongated tubing 18 and the valve stem 28 through to the valve stem connector 104 is filled with liquid from the bottle 14 seen in FIG. 1A by repeating the process described below.

Once the elongated tubing 18 and valve stem 18 are filled with water, it can be seen that the bottle check valve 26 is placed so that it firmly seals the bottle 14 from FIG. 1A and the elongated tubing 18 from the valve stem 28 and the stem opening 32 and the nozzle 30, preventing any liquid or gas from traveling from the valve stem 28 and the stem opening 32 through to the bottle 14 shown in FIG. 1A when a downward pressure is applied on the check valve 26 by depressing the spray button 24.

When the spray button 24 is depressed in a downstroke by a downward force applied by the user, liquid present in the valve stem 28 is forced through the only opening available, which is the stem opening 32 and the nozzle 30. When pressure is applied, the liquid easily pushes the nozzle check valve 106 out of place and flows past it to exit in a fine mist through the nozzle 30. Liquid is forced through the stem opening 32 and nozzle 30 as a result of the fact that the volume within the valve stem 28 and enclosing tube 112 is now decreased as a result of the depressing of the spray button 24, and the excess liquid must exist the vaporizing mechanism 22. When a downward force is applied by the user on the spray button 24 and depresses the spray button 24, the valve stem 28 pushes down on the valve stem resisting spring 84 and consequently compresses it.

After the spray button 24 is depressed, it is automatically returned to its original position in an upstroke by the decompressing of the valve stem resisting spring 84, which is caused by the spring 84 releasing the pressure from the downstroke that compressed it. This upstroke increases the volume in the valve stem 28 and the enclosing tube 112, and consequently creates an upward suction pressure within the vaporizing mechanism 22 that causes at once the nozzle check valve 106 to be pushed back into place, sealing the valve stem 28 and the enclosing tube 112 of the vaporizing mechanism 22 from the nozzle 30 and thereby preventing air from outside the vaporizing mechanism 22 to enter the vaporizing mechanism 22, and the bottle check valve 26 to be pulled out of place, thereby removing the seal between the bottle 14 from FIG. 1A and the elongated tubing 18 and the enclosing tube 112 and the valve stem 28, which allows liquid to flow from the elongated tubing 18 and the bottle 14 from FIG. 1A into the enclosing tube 112 and the valve stem 28 as a result of the upward suction pressure.

Consequently, while the downstroke causes liquid to be ejected from the valve stem 28 and the enclosing tube 112 through the nozzle 30, the upstroke causes liquid to be drawn up from the bottle 14 from FIG. 1A and the elongated tubing 18 into the valve stem 28 and the enclosing tube 112. This liquid drawn up from the upstroke replaces the liquid ejected from the downstroke in the valve stem 28 and the enclosing tube 112, thereby allowing this process of downstrokes and upstrokes to be repeated continuously until all the liquid in the bottle 14 shown in FIG. 1A has been ejected through the nozzle 30 in a fine mist.

Once all the liquid has been ejected from the bottle 14 shown in FIG. 1A, the bottle 14 shown in FIG. 1A may be refilled by unscrewing cap 20 and more specifically the inner bottom cap piece 94 from the bottle 14 shown in FIG. 1A, and then pouring more liquid into the bottle 14 shown in FIG. 1A via the opening in the top of the bottle 14 shown in FIG. 1A, and finally screwing the cap 20 and more specifically the inner bottom cap piece 94 back onto the bottle 14 shown in FIG. 1A. After this process is completed, the twist-up spray applicator 10 shown in FIG. 1A is ready to be reused.

There are two configurations of the twist-up spray applicator 10 from FIG. 1A: open and closed. In the open configuration the cap 20 is raised above the top of the outer enclosure 12 and hence the nozzle 30 is exposed and able to be aimed at the desired region of application and the spray button 24 is capable of being depressed. In the closed configuration the cap 20 is contained entirely within the metal enclosure 12 and the top of the cap 20 is flush with the top of the hollow outer enclosure 12.

To switch from the closed configuration to the open configuration, the user holds in one hand the outer casing bottom 38 shown in FIG. 1B and in the other hand holds the outer casing top 34 shown in the same figure. Then, the user twists the outer casing top 34 to the left while keeping the outer casing bottom 38 in place. As seen in FIG. 2, this causes the two protrusions 58 of the smaller inner bottom 50 piece to travel vertically upward along the two cut-out sections 46 of the larger inner bottom 42 piece, consequently causing the entire smaller inner bottom 50 piece to rise vertically. As the bottle 14 from FIG. 1A is held within the smaller inner bottom 50 piece, when the smaller inner bottom 50 piece rises, so too does the bottle 14 from FIG. 1A and the cap 20 from FIG. 1A which is attached to the top of the bottle 14 from FIG. 1A. Hence, by the action of this left twist, the applicator 10 from FIG. 1A is able to move from the closed configuration to the open configuration.

To move from the open configuration to the closed configuration, this operation is performed in reverse. As shown in FIG. 1B, the user holds the outer casing bottom 38 in one hand and in the other hand holds the outer casing top 34. Then, the user twists the outer casing top 34 to the right while keeping the outer casing bottom 38 in place. As seen in FIG. 2, this causes the two protrusions 58 of the smaller inner bottom 50 piece to travel vertically downward along the two cut-out sections 46 of the larger inner bottom 42 piece, consequently causing the entire smaller inner bottom 50 piece to fall vertically. As the bottle 14 from FIG. 1A is held in the smaller inner bottom 50 piece, when the smaller inner bottom 50 piece falls, so too does the bottle 14 from FIG. 1A and the cap 20 from FIG. 1A which is attached to the top of the bottle 14 from FIG. 1A. Hence, by the action of this right twist, the applicator 10 from FIG. 1A is able to move from the open configuration to the closed configuration.

Figure 3:
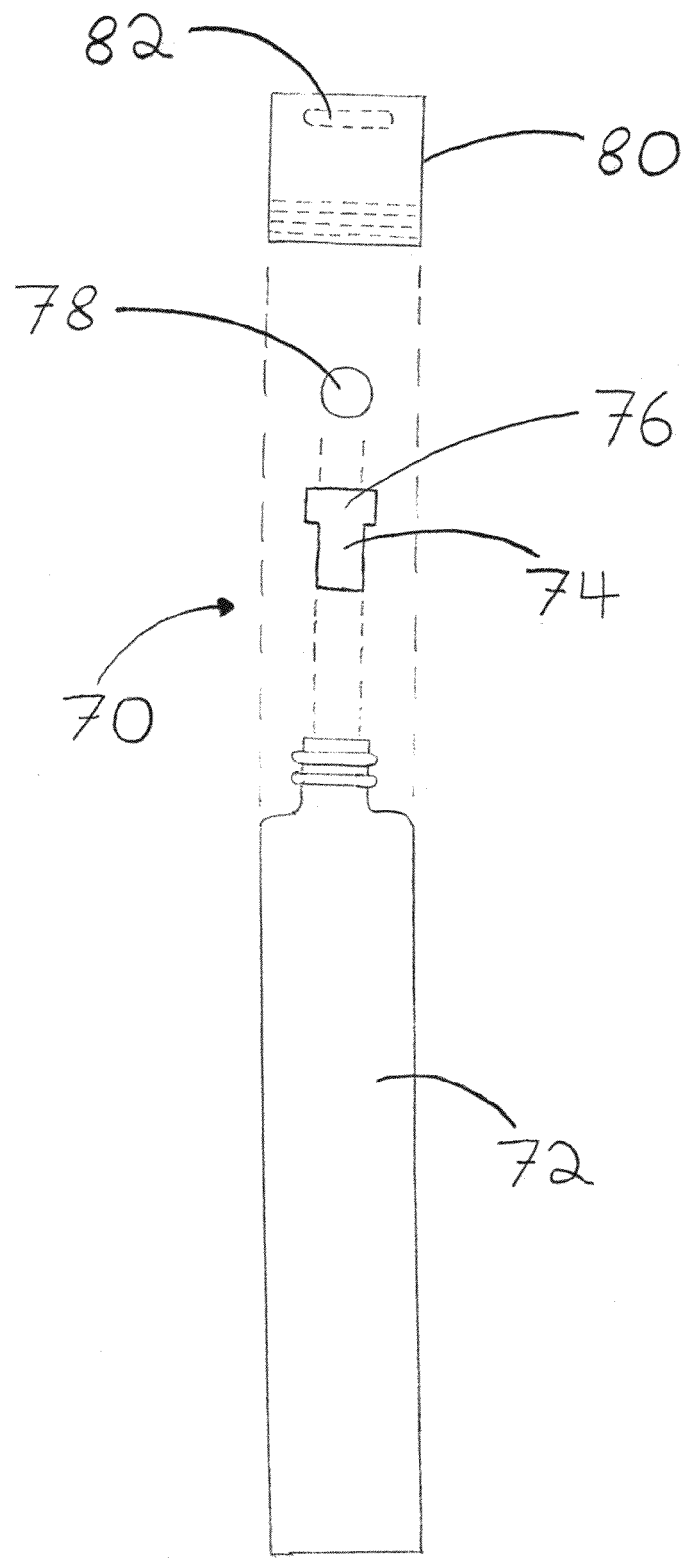
FIG. 3 shows a roll-on applicator embodiment of the apparatus for containing and transdermally applying a caffeine-containing composition.

Another embodiment of the apparatus including a caffeine-containing composition is illustrated in FIG. 3 (side view). There is shown a roll-on applicator 70 which as shown in FIG. 3 comprises a roll-on cylindrical bottle 72, made of glass, plastic such as polypropylene, metal such as steel or aluminum, or another suitable material, for containing a caffeine-containing composition that is attached to a plug connector 74, made of plastic such as polypropylene, metal such as steel or aluminum, or another suitable material, which in turn holds a rigid spherical ball 78, made of glass, metal such as steel or aluminum, or plastic such as polypropylene, or another suitable material, in its spherical basket 76 shaped groove. A roll-on cap 80, made of metal such as steel or aluminum, plastic such as polypropylene, or another suitable material, can be securely screwed on to the opening of the bottle 72. At the top of the cap 80, there is a spherical ball holding groove 82, which holds the top of the spherical ball 78 when the cap is screwed on to the bottle 72.

The manner of using this embodiment of the roll-on applicator 70 is shown in FIG. 3. In FIG. 3 it can be seen that the spherical ball 78 is held firmly in place by the plug connector 74, which in turn firmly plugs into the bottle opening. The plug connector 74 is hollow so that there is an open tube leading from the bottle 72 to the basket 76 to which the spherical ball 78 is attached. Hence, there is a direct path from the caffeine-containing composition held within the bottle 72 and the spherical ball 78, which allows the bottom of the spherical ball 78 to come in contact with the caffeine-containing composition by virtue of gravitational force when the roll-on applicator 70 is overturned and the bottle 72 is held above the spherical ball 78.

Hence, to operate the roll-on applicator 70 with the purpose of applying the caffeine-containing composition to the desired target region of skin, the user first removes the cap by twisting, and then holds the bottle 72 and overturns it so that the bottle 72 is held vertically above the spherical ball 78. This proceeds to coat the bottom of the spherical ball 78 with the caffeine-containing composition. Next, the user presses the spherical ball 78 against the desired target region of skin. Then, applying a slight amount of pressure so as to provide sufficient frictional force to rotate the spherical ball 78 within the basket 76, the user rolls the spherical ball 78 along the desired target region of skin back and forth, all the while applying sufficient pressure to ensure that the spherical ball 78 is rotating within the basket 76.

This movement will consequently apply the caffeine-containing composition to the skin as the part of the spherical ball 78 which is in contact with the caffeine-containing composition and thus coated in the composition will by virtue of the rotation be moved to be in contact with the desired target region of the skin. When it is in contact with the skin, it will transfer the caffeine-containing composition to the skin. At the same time, a part of the spherical ball 78 is always being coated with more caffeine-containing composition as it rotates, so that once the caffeine-containing composition has initially reached the skin and been successfully applied, a continuous stream of caffeine-containing composition will be carried to the skin by the rotating spherical ball 78 until the desired amount of caffeine has been applied, at which point the user may simply remove the spherical ball 78 from the skin, replace the cap 80 by twisting, and store the roll-on applicator 70 until needed again.

Figure 7:
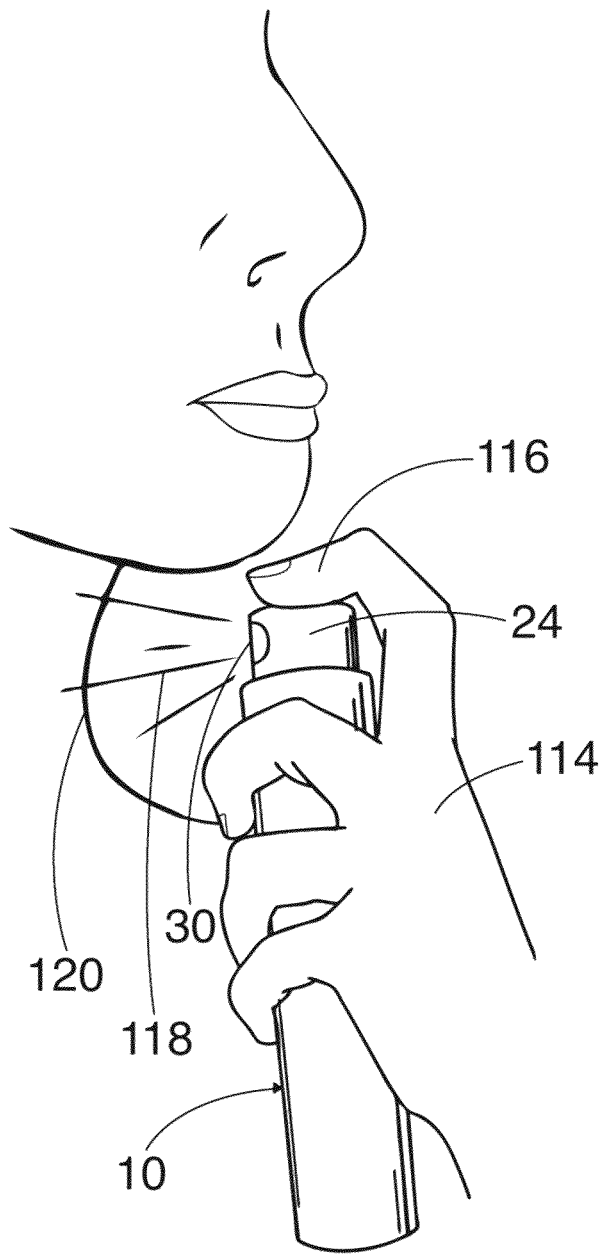
FIG. 7 shows an embodiment of a method of transdermal spray application of a caffeine-containing composition utilizing a spray applicator according to one embodiment.

One embodiment of a method of transdermal spray application of a caffeine composition utilizing a spray applicator embodiment of the apparatus including a caffeine composition is shown in FIG. 7. The spray applicator 10 is held in the open configuration by a user in a hand 114. The user then positions a finger 116 over the spray button 24 portion of the spray applicator 10, and aims the nozzle 30 of the spray applicator 10 towards a region of skin 120 where the user desires to apply the caffeine composition. The user then depresses the spray button 24, which causes a metered spray 118 of the caffeine composition to be ejected from the nozzle 30 of the spray applicator 10 and onto the desired region of skin 120. The user may then release pressure applied on the spray button 24 by their finger 116, which will cause the spray button 24 to rise from its depressed configuration and resume its original configuration. At this point, the user may repeat this method of transdermal spray application as many times as is needed to apply as much caffeine composition to the skin 120 as is desired.

In FIG. 7, the example region of skin 120 shown is on the neck, but this is only one particular region of skin 120 where the metered spray 118 of the caffeine composition may be applied, and there are many other regions of skin 120 where the caffeine composition may be applied. Examples of suitable locations on the skin 120 where the caffeine composition may be applied include, but are not limited to, the neck, upper back, wrists, and hip. It will be understood by one of ordinary skill in the art that these body parts are listed due to their proximity to the bloodstream, accessibility, and relatively reduced fat accumulation, among other factors.

V. ADVANTAGES

In one or more embodiments, the solubility and skin penetration rate of the caffeine in the caffeine-containing compositions is greatly increased over the normal solubility and skin penetration rate of pure caffeine in aqueous solution. This allows for much more caffeine to be applied to a target region of skin than was previously possible with a pure caffeine aqueous solution application. This also allows for the caffeine to penetrate the skin at an increased rate, thus further increasing the physiological effect that the transdermally applied caffeine may have on a user. These improvements to the solubility and skin penetration rate of caffeine make the compositions of one or more embodiments viable to a wide range of users, some of whom may desire or require as a consequence of increased caffeine tolerance more caffeine to be transdermally applied than is practically feasible through a pure caffeine aqueous solution application.

Being highly concentrated, dozens of applications of the compositions can be stored in a small, portable container in one or more embodiments. This container can easily be held in a pocket, purse, or bag, thus allowing a user to always have a source of the caffeine-containing composition with them at all times. This eliminates the possibility that users will ever find themselves in a situation where they require the stimulatory effects of the caffeine-containing composition but have none of it available. Also, due to the highly concentrated and multi-application nature of one or more embodiments, it is possible to provide users with a much more affordable and cost-effective long-term caffeine administration solution than most highly diluted single-use caffeine-containing drinks currently on the market.

In addition, the bitter taste of caffeine is avoided in one or more embodiments, as the caffeine-containing composition does not enter contact with the tongue at any point. This allows those who desire the stimulatory effects of caffeine but dislike the bitter taste of caffeine to take advantage of its benefits. One or more embodiments also preclude the possibility of staining the teeth or clothing, as they do not come in contact with the teeth and are colorless. One or more embodiments also preclude the possibility of halitosis, as they do not come in contact with the mouth and/or are odorless.

I have also discovered that in one or more embodiments, after the solvents have fully evaporated, caffeine will at most form a thin film on the skin that is not sticky or messy and may easily be wiped off with a finger. Consequently, a liquid composition formulation of caffeine is advantageous to gel or patch formulations, which often impart sticky and messy residues on the skin.

Furthermore, in one or more embodiments, intake of the caffeine-containing composition is carefully regulated. Once the caffeine-containing composition is applied to the skin, the composition permeates the skin at a steady rate as opposed to permeating all at once. This prevents the effect experienced with orally ingested or intravenously ingested caffeine, where a large amount of the caffeine is absorbed into the body at the same time. Having a steady rate of permeation as opposed to absorbing all the caffeine at once is desirable as it helps deliver the stimulatory effects of caffeine smoothly over several hours, at once prolonging the effect of the caffeine and also mitigating the risk of overdose from absorbing more caffeine than desirable at one time.

In one or more embodiments, the method of application is also much quicker and simpler than many other methods such as ingestion or injection. In one or more embodiments the apparatus for applying the caffeine-containing composition incorporates a twist-up spray nozzle or a roll-on applicator. These apparatuses allow application of the caffeine-containing composition in one simple step. This is unlike ingestion, which requires intake over a relatively long period of time, or injection, which is uncomfortable and complicated.

Moreover, in one or more embodiments, the method of application allows the user to control the amount of caffeine applied by varying the number of applications. Unlike caffeine containing drinks, which encourage the imbiber to consume a set amount of liquid and caffeine, this method encourages the user to regulate each dose so that they only receive the amount of stimulation they desire from the caffeine, and do not overdose.

VI. CONCLUSIONS, RAMIFICATIONS, AND SCOPE

Accordingly, the reader will see that one or more aspects provide a quick and simple solution for applying caffeine in a portable, multi-application apparatus. It is evident that one or more embodiments demonstrate a method of application that is palatable to those who do not enjoy the bitter taste of caffeine, and is also odorless and will not contribute to halitosis, unlike coffee and other caffeine-containing drinks. In one or more aspects the apparatus allows the user to control the dose applied, and along with the method of application in one or more aspects, this mitigates the risk of overdose as only a steady rate of caffeine may permeate the skin at any given time.

In one or more embodiments, the solubility and skin penetration rate of the caffeine in the caffeine-containing compositions is also greatly increased, thereby making the compositions of one or more embodiments viable to a wide range of users, some of whom may desire or require as a consequence of increased caffeine tolerance more caffeine to be transdermally applied than is practically feasible through a pure caffeine aqueous solution application.

Although the description above contains much specificity, these should not be construed as limiting the scope of the embodiments but as merely providing illustrations of some of several embodiments. For example, a caffeine-containing composition may be applied with other apparatuses, such as a spray applicator that does not twist up but is covered with a removable cap, or a reservoir and cloth system where the cloth is dipped into a caffeine-containing composition and applied to the desired skin region. A caffeine-containing composition may also include other ingredients, such as the addition of peppermint or a menthol derivative to provide a pleasant scent and a cooling sensation as a mechanism to signal to the user that the composition has been successfully applied, or the use of alcohol to aid as a solvent for certain other ingredients. A caffeine-containing composition may also include different ingredients to aid in increasing solubility, such as citric acid and other suitable acids.

Thus the scope of the embodiments should be determined by the appended claims and their legal equivalents, rather than by the examples given.

VII. EXAMPLES

Example 1

The Preparation of Tryptophan Isopropyl Ester.HCl

Tryptophan (1 kg) was suspended in isopropanol (5 L) in a 10 L flask. HCl gas (350 g) was bubbled into the reaction mixture. The mixture was stirred for 2 days at 50° C. The solvent was evaporated off at below 40° C., and fresh isopropanol (4 L) was added into the residue. The mixture was stirred for 1 day at 50° C. The solvent was evaporated off at below 40° C., and isopropyl acetate (3 L) was added into the residue. The solid was collected by filtration and washed with isopropyl acetate (3×1 L). The solid was dried in a vacuum oven at 50° C.

Example 2

The Preparation of D-Tryptophan Isopropyl Ester.HCl

D-Tryptophan (1 kg) was suspended in isopropanol (5 L) in a 10 L flask. HCl gas (350 g) was bubbled into the reaction mixture. The mixture was stirred for 2 days at 50° C. The solvent was evaporated off at below 40° C., and fresh isopropanol (4 L) was added into the residue. The mixture was stirred for 1 day at 50° C. The solvent was evaporated off at below 40° C., and isopropyl acetate (3 L) was added into the residue. The solid was collected by filtration and washed with isopropyl acetate (3×1 L). The solid was dried in a vacuum oven at 50° C.

All other esters of amino acids can be prepared by a similar method.

Example 3

Preparation of 2-(diethylamino)ethyl 2-(4-isobutylphenyl)propionate hydrochloride 2-(4-isobutylphenyl)propionoic acid (4120 g) was dissolved in ethyl acetate (R0061, 4 L) and thionyl chloride (1750 ml). The mixture was refluxed for 3 h. The mixture was evaporated to dryness completely. Isopropyl acetate (3 L) was added into the residue and the mixture was evaporated to dryness. Isopropyl acetate (3 L) was added into the residue and evaporated off. Isopropyl acetate (20 L) was added into the reaction mixture. The mixture was cooled to 5° C. in an ice-water bath. N,N-diethylaminoethanol (2340 g) was added into the reaction mixture drop by drop. $K_2CO_3$ (2800 g) was added into the reaction mixture slowly. The mixture was stirred overnight at room temperature. Water (10 L) was added into the mixture. The ethyl acetate mixture was collected and washed with 5% $NaHCO_3$ (1×7 L) and water (3×6 L) and dried over $Na_2SO_4$. Sodium sulfate was removed by filtration and washed with isopropyl acetate (3×1 L). HCl gas (700 g) was added into the mixture and stirred. The solid was collected and washed with isopropyl acetate (3×2 L). The product was dried in a vacuum oven at 45° C.

All (dialkylamino)ethyl 2-(4-isobutylphenyl)propionate hydrochlorides, 2-(dialkylamino)alkyl 2-acetoxybenzoate hydrochlorides, and other esters can be prepared by a similar method.

Example 4

The Preparation of Composition 1

Tryptophan ethyl ester.HCl (120 g) was dissolved in water (1 L). Caffeine (100 g) was added into the mixture and the mixture was stirred for a few minutes. The mixture was filled into either spray bottles or roll-on bottles.

Example 5

The Preparation of Composition 2

D-Tryptophan ethyl ester.HCl (120 g) was dissolved in water (1 L). Caffeine (100 g) was added into the mixture and the mixture was stirred for a few minutes. The mixture was filled into either spray bottles or roll-on bottles.

Example 6

The Preparation of Composition 3

Tryptophan isopropyl ester.HBr (120 g) was dissolved in water (1 L). Caffeine (100 g) and menthol (10 g) were added into the mixture and the mixture was stirred for a few minutes. The mixture was filled into either spray bottles or roll-on bottles.

Example 7

The Preparation of Composition 4

Tryptophan isopropyl ester.lactic acid (120 g) was dissolved in water (1 L). Caffeine (100 g), menthol (20 g) and ethanol (100 ml) were added into the mixture and the mixture was stirred for a few minutes. The mixture was filled into either spray bottles or roll-on bottles.

Example 8

The Preparation of Composition 5

Tryptophan isopropyl ester.HCl (70 g) was dissolved in water (1 L). Caffeine (60 g) and menthol (20 g) were added into the mixture and the mixture was stirred for a few minutes. The mixture was filled into either spray bottles or roll-on bottles.

Example 9

The Preparation of Composition 6

Leucine isopropyl ester.HCl (100 g) was dissolved in water (1 L). Caffeine (30 g) and menthol (5 g) were added into the mixture and the mixture was stirred for a few minutes. The mixture was filled into either spray bottles or roll-on bottles.

Example 10

The Preparation of Composition 7

Isoleucine isopropyl ester.HCl (100 g) was dissolved in water (1 L). Caffeine (30 g) and menthol (8 g) were added into the mixture and the mixture was stirred for a few minutes. The mixture was filled into either spray bottles or roll-on bottles.

Example 11

The Preparation of Composition 8

Tyrosine isopropyl ester.HCl (120 g) was dissolved in water (1 L). Caffeine (100 g) and menthol (20 g) were added into the mixture and the mixture was stirred for a few minutes. The mixture was filled into either spray bottles or roll-on bottles.

Example 12

The Preparation of Composition 9

Tyrosine isopropyl ester.HCl (70 g) was dissolved in water (1 L). Caffeine (60 g) and menthol (10 g) were added into the mixture and the mixture was stirred for a few minutes. The mixture was filled into either spray bottles or roll-on bottles.

Example 13

The Preparation of Composition 10

Tyrosine isopropyl ester.HCl (70 g) was dissolved in water (1 L). Caffeine (50 g), ethanol (100 ml) and menthol (20 g) were added into the mixture and the mixture was stirred for a few minutes. The mixture was filled into either spray bottles or roll-on bottles.

Example 14

The Preparation of Composition 11

Proline ethyl ester.HCl (100 g) was dissolved in water (1 L). Caffeine (30 g) and menthol (5 g) were added into the mixture and the mixture was stirred for a few minutes. The mixture was filled into either spray bottles or roll-on bottles.

Example 15

The Preparation of Composition 12

Tyrosine isopropyl ester.HCl (70 g) and tyrosine (7 g) were dissolved in water (1 L). Caffeine (50 g), ethanol (100 ml) and menthol (20 g) were added into the mixture and the mixture was stirred for a few minutes. The mixture was filled into either spray bottles or roll-on bottles.

Example 16

The Preparation of Composition 13

Tyrosine isopropyl ester.HCl (70 g) and tyrosine (7 g) were dissolved in water (1 L). Caffeine (50 g) and menthol (10 g) were added into the mixture and the mixture was stirred for a few minutes. The mixture was filled into either spray bottles or roll-on bottles.

Example 17

The Preparation of Composition 14

Tryptophan isopropyl ester.HBr (120 g) and tryptophan (5 g) were dissolved in water (1 L). Caffeine (100 g) and menthol (10 g) were added into the mixture and the mixture was stirred for a few minutes. The mixture was filled into either spray bottles or roll-on bottles.

Example 18

The Preparation of Composition 15

Valine ethyl ester.HCl (100 g) was dissolved in water (1 L). Caffeine (30 g), DMSO (200 ml), and menthol (30 g) were added into the mixture and the mixture was stirred for a few minutes. The mixture was filled into either spray bottles or roll-on bottles.

Example 19

The Preparation of Composition 16

Valine ethyl ester.HCl (100 g) was dissolved in water (1 L). Caffeine (30 g), DMSO (200 ml), and menthol (30 g) were added into the mixture and the mixture was stirred for a few minutes. The mixture was filled into either spray bottles or roll-on bottles.

Example 20

The Preparation of Composition 17

Phenylalanine butyl ester.HCl (100 g) was dissolved in water (1 L). Caffeine (30 g), glycerin (200 ml), and menthol (30 g) were added into the mixture and the mixture was stirred for a few minutes. The mixture was filled into either spray bottles or roll-on bottles.

Example 21

The Preparation of Composition 18

Phenylalanine butyl ester.HCl (100 g) was dissolved in water (1 L). Caffeine (30 g), sodium benzoate (50 g), and menthol (30 g) were added into the mixture and the mixture was stirred for a few minutes. The mixture was filled into either spray bottles or roll-on bottles.

Example 22

The Preparation of Composition 19

2-(diethylamino)propyl 2-acetoxybenzoate hydrochloride (100 g) was dissolved in water (1 L). Caffeine (80 g), glycerin (200 ml), and menthol (30 g) were added into the mixture and the mixture was stirred for a few minutes. The mixture was filled into either spray bottles or roll-on bottles.

Example 23

The Preparation of Composition 20

2-(diethylamino)propyl 2-acetoxybenzoate hydrochloride (70 g) was dissolved in water (1 L). Caffeine (60 g), and menthol (10 g) were added into the mixture and the mixture was stirred for a few minutes. The mixture was filled either into spray bottles or roll-on bottles.

Example 24

The Preparation of Composition 21

Tryptophan isopropyl ester.HBr (120 g) was dissolved in water (1 L). Caffeine (100 g) was added into the mixture and the mixture was stirred for a few minutes. The mixture was filled into either spray bottles or roll-on bottles.

Example 25

The Preparation of Composition 22

Tryptophan isopropyl ester.lactic acid (120 g) was dissolved in water (1 L). Caffeine (100 g) was added into the mixture and the mixture was stirred for a few minutes. The mixture was filled into either spray bottles or roll-on bottles.

Example 26

The Preparation of Composition 23

Tryptophan isopropyl ester.HCl (70 g) was dissolved in water (1 L). Caffeine (60 g) was added into the mixture and the mixture was stirred for a few minutes. The mixture was filled into either spray bottles or roll-on bottles.

Example 27

The Preparation of Composition 24

Leucine isopropyl ester.HCl (100 g) was dissolved in water (1 L). Caffeine (30 g) was added into the mixture and the mixture was stirred for a few minutes. The mixture was filled into either spray bottles or roll-on bottles.

Example 28

The Preparation of Composition 25

Isoleucine isopropyl ester.HCl (100 g) was dissolved in water (1 L). Caffeine (30 g) was added into the mixture and the mixture was stirred for a few minutes. The mixture was filled into either spray bottles or roll-on bottles.

Example 29

The Preparation of Composition 26

Tyrosine isopropyl ester.HCl (120 g) was dissolved in water (1 L). Caffeine (100 g) was added into the mixture and the mixture was stirred for a few minutes. The mixture was filled into either spray bottles or roll-on bottles.

Example 30

The Preparation of Composition 27

Tyrosine isopropyl ester.HCl (70 g) was dissolved in water (1 L). Caffeine (60 g) was added into the mixture and the mixture was stirred for a few minutes. The mixture was filled into either spray bottles or roll-on bottles.

Example 31

The Preparation of Composition 28

Tyrosine isopropyl ester.HCl (70 g) was dissolved in water (1 L). Caffeine (50 g) was added into the mixture and the mixture was stirred for a few minutes. The mixture was filled into either spray bottles or roll-on bottles.

Example 32

The Preparation of Composition 29

Proline ethyl ester.HCl (100 g) was dissolved in water (1 L). Caffeine (30 g) was added into the mixture and the mixture was stirred for a few minutes. The mixture was filled into either spray bottles or roll-on bottles.

Example 33

The Preparation of Composition 30

Tyrosine isopropyl ester.HCl (70 g) and tyrosine (7 g) were dissolved in water (1 L). Caffeine (50 g) was added into the mixture and the mixture was stirred for a few minutes. The mixture was filled into either spray bottles or roll-on bottles.

Example 34

The Preparation of Composition 31

Tyrosine isopropyl ester.HCl (70 g) and tyrosine (7 g) were dissolved in water (1 L). Caffeine (50 g) was added into the mixture and the mixture was stirred for a few minutes. The mixture was filled into either spray bottles or roll-on bottles.

Example 35

The Preparation of Composition 32

Tryptophan isopropyl ester.HBr (120 g) and tryptophan (5 g) were dissolved in water (1 L). Caffeine (100 g) was added into the mixture and the mixture was stirred for a few minutes. The mixture was filled into either spray bottles or roll-on bottles.

Example 36

The Preparation of Composition 33

Valine ethyl ester.HCl (100 g) was dissolved in water (1 L). Caffeine (30 g) was added into the mixture and the mixture was stirred for a few minutes. The mixture was filled into either spray bottles or roll-on bottles.

Example 37

The Preparation of Composition 34

Valine ethyl ester.HCl (100 g) was dissolved in water (1 L). Caffeine (30 g) was added into the mixture and the mixture was stirred for a few minutes. The mixture was filled into either spray bottles or roll-on bottles.

Example 38

The Preparation of Composition 35

Phenylalanine butyl ester.HCl (100 g) was dissolved in water (1 L). Caffeine (30 g) and glycerin (200 ml) were added into the mixture and the mixture was stirred for a few minutes. The mixture was filled into either spray bottles or roll-on bottles.

Example 39

The Preparation of Composition 36

Phenylalanine butyl ester.HCl (100 g) was dissolved in water (1 L). Caffeine (30 g) and sodium benzoate (50 g) were added into the mixture and the mixture was stirred for a few minutes. The mixture was filled into either spray bottles or roll-on bottles.

Example 40

The Preparation of Composition 37

2-(diethylamino)propyl 2-acetoxybenzoate hydrochloride (100 g) was dissolved in water (1 L). Caffeine (80 g) and glycerin (200 ml) were added into the mixture and the mixture was stirred for a few minutes. The mixture was filled into either spray bottles or roll-on bottles.

Example 41

Solubility of Caffeine in Certain Caffeine-Containing Compositions Containing Various Helper Esters Caffeine solubility was obtained for various caffeine-containing compositions containing various helper esters. Results are shown in Tables 1-9.

TABLE 1

Solubility of caffeine (%, w/v) in tryptophan esters

| | Solubility of caffeine (w/v) |
|---|---|
| 6% tryptophan isopropyl ester hydrochloride in water at 20° C. | >6% |
| 6% D-tryptophan isopropyl ester hydrochloride in water at 20° C. | >6% |
| 10% tryptophan isopropyl ester hydrochloride in water at 20° C. | >10% |
| 10% D-tryptophan isopropyl ester hydrochloride in water at 20° C. | >10% |
| 10% tryptophan ethyl ester hydrochloride in water at 20° C. | >10% |
| 10% D-tryptophan ethyl ester hydrochloride in water at 20° C. | >10% |
| 10% tryptophan butyl ester hydrochloride in water at 20° C. | >8% |
| 10% D-tryptophan butyl ester hydrochloride in water at 20° C. | >8% |
| 6% tryptophan isopropyl ester hydrochloride in water at 10° C. | >5% |
| 6% D-tryptophan isopropyl ester hydrochloride in water at 10° C. | >5% |
| 10% tryptophan isopropyl ester hydrochloride in water at 10° C. | >8% |
| 10% D-tryptophan isopropyl ester hydrochloride in water at 10° C. | >8% |
| 10% tryptophan ethyl ester hydrochloride in water at 10° C. | >8% |
| 10% D-tryptophan ethyl ester hydrochloride in water at 10° C. | >8% |
| 10% tryptophan butyl ester hydrochloride in water at 10° C. | >7% |
| 10% D-tryptophan butyl ester hydrochloride in water at 10° C. | >7% |

TABLE 2

Solubility of caffeine (%, w/v) in leucine esters

| | Solubility of caffeine (w/v) |
|---|---|
| 6% leucine isopropyl ester hydrochloride in water at 20° C. | >3% |
| 10% leucine isopropyl ester hydrochloride in water at 20° C. | >4% |
| 10% leucine methyl ester hydrochloride in water at 20° C. | >4% |
| 10% leucine hexyl ester hydrochloride in water at 20° C. | >3% |
| 6% leucine isopropyl ester hydrochloride in water at 10° C. | >2.5% |
| 10% leucine isopropyl ester hydrochloride in water at 10° C. | >3% |
| 10% leucine methyl ester hydrochloride in water at 10° C. | >3% |
| 10% leucine hexyl ester hydrochloride in water at 10° C. | >2.5% |

TABLE 3

Solubility of caffeine (%, w/v) in isoleucine esters

| | Solubility of caffeine (w/v) |
|---|---|
| 6% isoleucine isopropyl ester hydrochloride in water at 20° C. | >3% |
| 10% isoleucine isopropyl ester hydrochloride in water at 20° C. | >4% |
| 10% isoleucine methyl ester hydrochloride in water at 20° C. | >4% |
| 10% isoleucine hexyl ester hydrochloride in water at 20° C. | >3% |
| 6% isoleucine isopropyl ester hydrochloride in water at 10° C. | >2.5% |
| 10% isoleucine isopropyl ester hydrochloride in water at 10° C. | >3% |
| 10% isoleucine methyl ester hydrochloride in water at 10° C. | >3% |
| 10% isoleucine hexyl ester hydrochloride in water at 10° C. | >2.5% |

TABLE 4

Solubility of caffeine (%, w/v) in tyrosine esters

| | Solubility of caffeine (w/v) |
|---|---|
| 6% tyrosine isopropyl ester hydrochloride in water at 20° C. | >5% |
| 10% tyrosine isopropyl ester hydrochloride in water at 20° C. | >9% |
| 10% tyrosine propyl ester hydrochloride in water at 20° C. | >9% |
| 10% tyrosine pentyl ester hydrochloride in water at 20° C. | >9% |
| 6% tyrosine isopropyl ester hydrochloride in water at 10° C. | >4% |
| 10% tyrosine isopropyl ester hydrochloride in water at 10° C. | >7% |
| 10% tyrosine propyl ester hydrochloride in water at 10° C. | >7% |
| 10% tyrosine pentyl ester hydrochloride in water at 10° C. | >7% |

TABLE 5

Solubility of caffeine (%, w/v) in phenylalanine esters

| | Solubility of caffeine (w/v) |
|---|---|
| 6% phenylalanine isopropyl ester hydrochloride in water at 20° C. | >3% |
| 10% phenylalanine isopropyl ester hydrochloride in water at 20° C. | >4% |
| 10% phenylalanine methyl ester hydrochloride in water at 20° C. | >4% |
| 10% phenylalanine octyl ester hydrochloride in water at 20° C. | >3% |
| 6% phenylalanine isopropyl ester hydrochloride in water at 10° C. | >2.5% |
| 10% phenylalanine isopropyl ester hydrochloride in water at 10° C. | >3% |
| 10% phenylalanine methyl ester hydrochloride in water at 10° C. | >3% |
| 10% phenylalanine octyl ester hydrochloride in water at 10° C. | >2.5% |

TABLE 6

Solubility of caffeine (%, w/v) in proline esters

| | Solubility of caffeine (w/v) |
|---|---|
| 6% proline isopropyl ester hydrochloride in water at 20° C. | >3% |
| 10% proline isopropyl ester hydrochloride in water at 20° C. | >4% |
| 10% proline methyl ester hydrochloride in water at 20° C. | >4% |
| 10% proline hexyl ester hydrochloride in water at 20° C. | >3% |
| 6% proline isopropyl ester hydrochloride in water at 10° C. | >2.5% |
| 10% proline isopropyl ester hydrochloride in water at 10° C. | >3% |
| 10% proline methyl ester hydrochloride in water at 10° C. | >3% |
| 10% proline hexyl ester hydrochloride in water at 10° C. | >3% |

TABLE 7

Solubility of caffeine (%, w/v) in 2-(Dialkylamino)alkyl 2-acetoxybenzoate hydrochloride (non-amino acid esters)

| | Solubility of caffeine (w/v) |
|---|---|
| 6% 2-(diethylamino)propyl 2-acetoxybenzoate hydrochloride in water at 20° C. | >5% |
| 10% 2-(diethylamino)propyl 2-acetoxybenzoate hydrochloride in water at 20° C. | >9% |
| 10% 2-(dimethylamino)hexyl 2-acetoxybenzoate hydrochloride in water at 20° C. | >9% |
| 10% 2-(dibutylamino)ethyl 2-acetoxybenzoate hydrochloride in water at 20° C. | >9% |
| 6% 2-(diethylamino)propyl 2-acetoxybenzoate hydrochloride in water at 10° C. | >4% |
| 10% 2-(diethylamino)ethyl 2-acetoxybenzoate hydrochloride in water at 10° C. | >7% |
| 10% 2-(dimethylamino)ethyl 2-acetoxybenzoate hydrochloride in water at 10° C. | >7% |
| 10% 2-(dibutylamino)ethyl 2-acetoxybenzoate hydrochloride in water at 10° C. | >7% |

TABLE 8

Solubility of caffeine (%, w/v) in 2-(Dialkylamino)ethyl 2-(4-isobutylphenyl)propionate hydrochloride (acid esters that are not esters of natural amino acids)

| | Solubility of caffeine (w/v) |
|---|---|
| 6% 2-(Diethylamino)pentyl 2-(4-isobutylphenyl)propionate hydrochloride in water at 20° C. | >3% |
| 10% 2-(Diethylamino)pentyl 2-(4-isobutylphenyl)propionate hydrochloride in water at 20° C. | >4% |
| 10% 2-(Dimethylamino)ethyl 2-(4-isobutylphenyl)propionate hydrochloride in water at 20° C. | >4% |
| 10% 2-(Dipentylamino)methyl 2-(4-isobutylphenyl)propionate hydrochloride in water at 20° C. | >3% |
| 6% 2-(Diethylamino)ethyl 2-(4-isobutylphenyl)propionate hydrochloride in water at 10° C. | >2.5% |
| 10% 2-(Diethylamino)butyl 2-(4-isobutylphenyl)propionate hydrochloride in water at 10° C. | >3% |
| 10% 2-(Dimethylamino)propyl 2-(4-isobutylphenyl)propionate hydrochloride in water at 10° C. | >3% |
| 10% 2-(Dipentylamino)ethyl 2-(4-isobutylphenyl)propionate hydrochloride in water at 10° C. | >2.5% |

TABLE 9

Effects of Acids (HA) of esters of amino acids and other acids on the solubility of caffeine

| | Solubility of caffeine (w/v) |
|---|---|
| 10% tryptophan isopropyl ester hydrochloride (tryptophan isopropyl ester•HCl) in water at 20° C. | >10% |
| 10% tryptophan isopropyl ester•HF in water at 20° C. | >10% |
| 10% tryptophan isopropyl ester•HBr in water at 20° C. | >10% |
| 10% tryptophan isopropyl ester•HCl in water at 20° C. | >10% |
| 10% tryptophan isopropyl ester•citric acid in water at 20° C. | >9% |
| 10% tryptophan isopropyl ester•acetic acid in water at 20° C. | >9% |
| 10% tryptophan isopropyl ester•benzoic acid in water at 20° C. | >9% |
| 10% tryptophan isopropyl ester•lactic acid in water at 20° C. | >10% |

Example 42

Figure 5A:
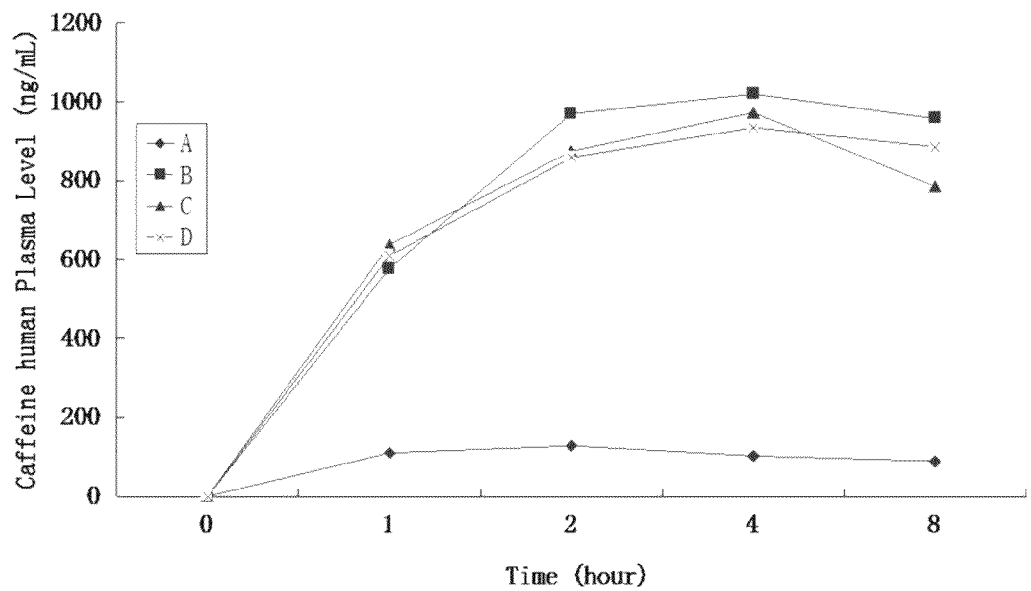
FIGS. 5A-5H show the effects of some esters on the human skin penetration rate of caffeine.

Transdermal Delivery of Caffeine Using Certain Caffeine-Containing Compositions Disclosed Herein FIG. 5A shows effects of tryptophan esters.HCl on transdermal delivery of caffeine in human. A: 1.05 ml of 2% caffeine in water was applied to skin on the neck of the body (20 cm×20 cm); B: 0.35 ml of 7% tryptophan isopropyl ester.HCl and 6% caffeine in water was applied to skin on the back of the body (20 cm×20 cm); C: 0.35 ml of 7% tryptophan ethyl ester.HCl and 6% caffeine in water was applied to skin on the back of the body (20 cm×20 cm); D: 0.35 ml of 7% tryptophan butyl ester.HCl and 6% caffeine in water was applied to skin on the back of the body (20 cm×20 cm).

Figure 5B:
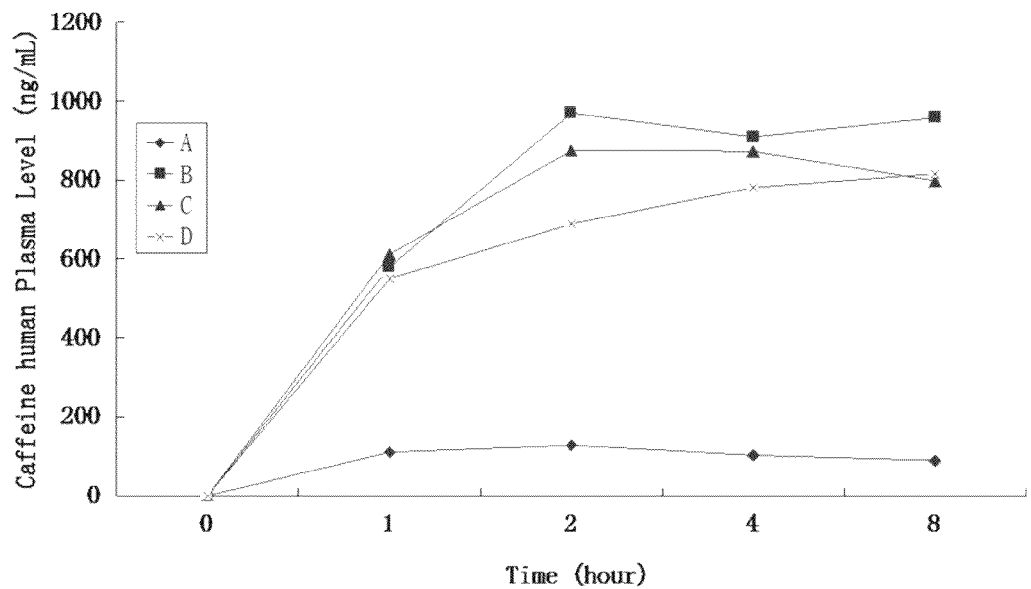

FIG. 5B shows effects of leucine esters.HCl on transdermal delivery of caffeine in human. A: 1.05 ml of 2% caffeine in water was applied to skin on the neck of the body (20 cm×20 cm); B: 0.70 ml of 7% leucine isopropyl ester.HCl and 3% caffeine in water was applied to skin on the back of the body (20 cm×20 cm); C: 0.70 ml of 7% leucine methyl ester.HCl and 3% caffeine in water was applied to skin on the back of the body (20 cm×20 cm); D: 0.70 ml of 7% leucine hexyl ester.HCl and 3% caffeine in water was applied to skin on the back of the body (20 cm×20 cm).

Figure 5C:
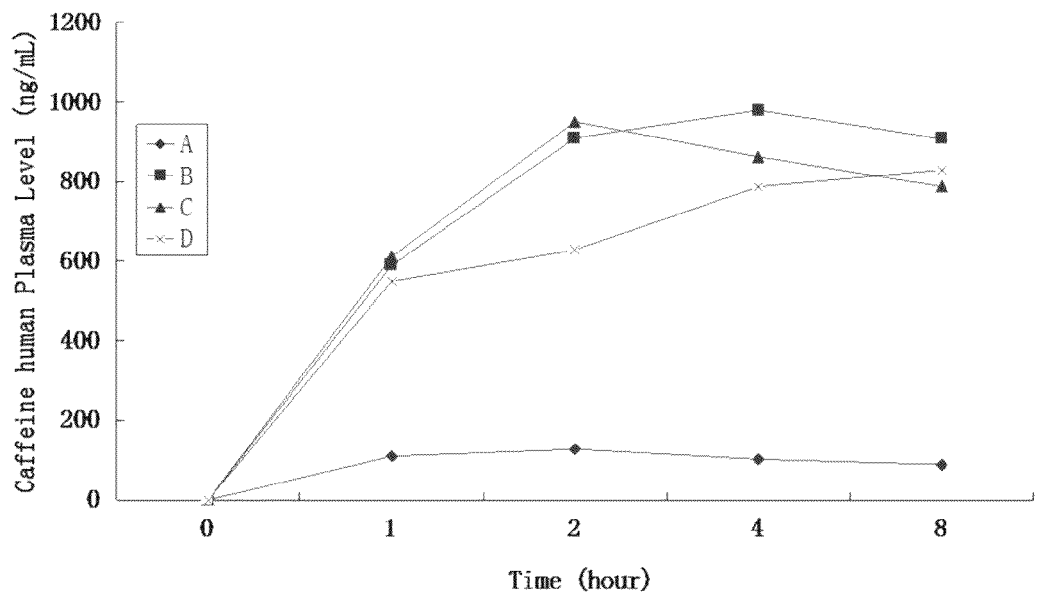

FIG. 5C shows effects of isoleucine esters on transdermal delivery of caffeine in human. A: 1.05 ml of 2% caffeine in water was applied to skin on the neck of the body (20 cm×20 cm); B: 0.70 ml of 7% isoleucine isopropyl ester and 3% caffeine in water was applied to skin on the back of the body (20 cm×20 cm); C: 0.70 ml of 7% isoleucine methyl ester and 3% caffeine in water was applied to skin on the back of the body (20 cm×20 cm); D: 0.70 ml of 7% isoleucine hexyl ester and 3% caffeine in water was applied to skin on the back of the body (20 cm×20 cm).

Figure 5D:
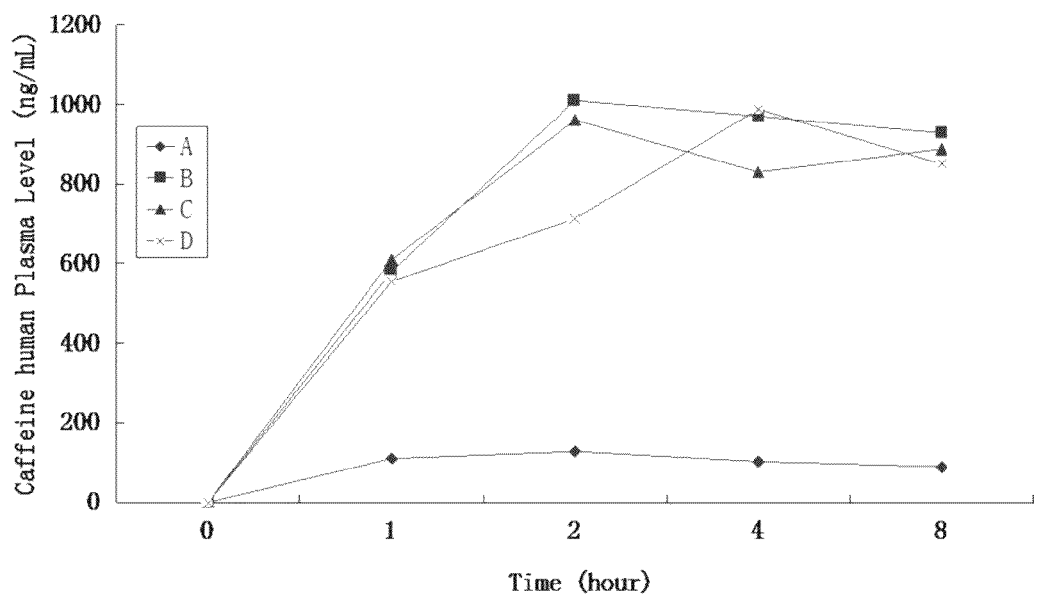

FIG. 5D shows effects of tyrosine esters on transdermal delivery of caffeine in human. A: 1.05 ml of 2% caffeine in water was applied to skin on the neck of the body (20 cm×20 cm); B: 0.35 ml of 7% tyrosine isopropyl ester and 6% caffeine in water was applied to skin on the back of the body (20 cm×20 cm); C: 0.35 ml of 7% tyrosine propyl ester and 6% caffeine in water was applied to skin on the back of the body (20 cm×20 cm); D: 0.35 ml of 7% tyrosine pentyl ester and 6% caffeine in water was applied to skin on the back of the body (20 cm×20 cm).

Figure 5E:
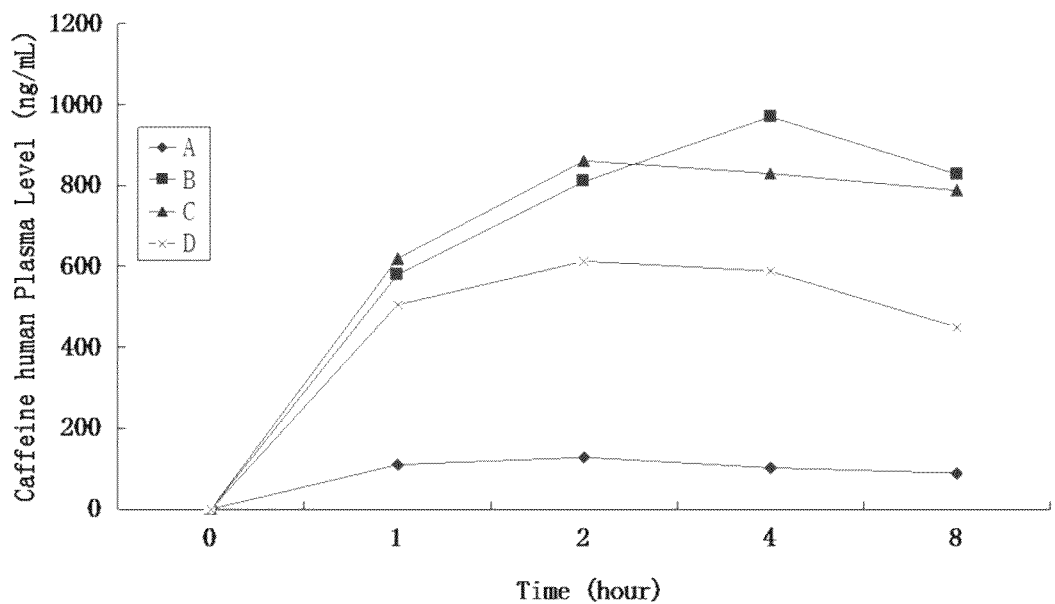

FIG. 5E shows effects of phenylalanine esters.HCl on transdermal delivery of caffeine in human. A: 1.05 ml of 2% caffeine in water was applied to skin on the neck of the body (20 cm×20 cm); B: 0.70 ml of 7% phenylalanine isopropyl ester.HCl and 3% caffeine in water was applied to skin on the back of the body (20 cm×20 cm); C: 0.70 ml of 7% phenylalanine methyl ester.HCl and 3% caffeine in water was applied to skin on the back of the body (20 cm×20 cm); D: 0.70 ml of 7% phenylalanine octyl ester.HCl and 3% caffeine in water was applied to skin on the back of the body (20 cm×20 cm).

Figure 5F:
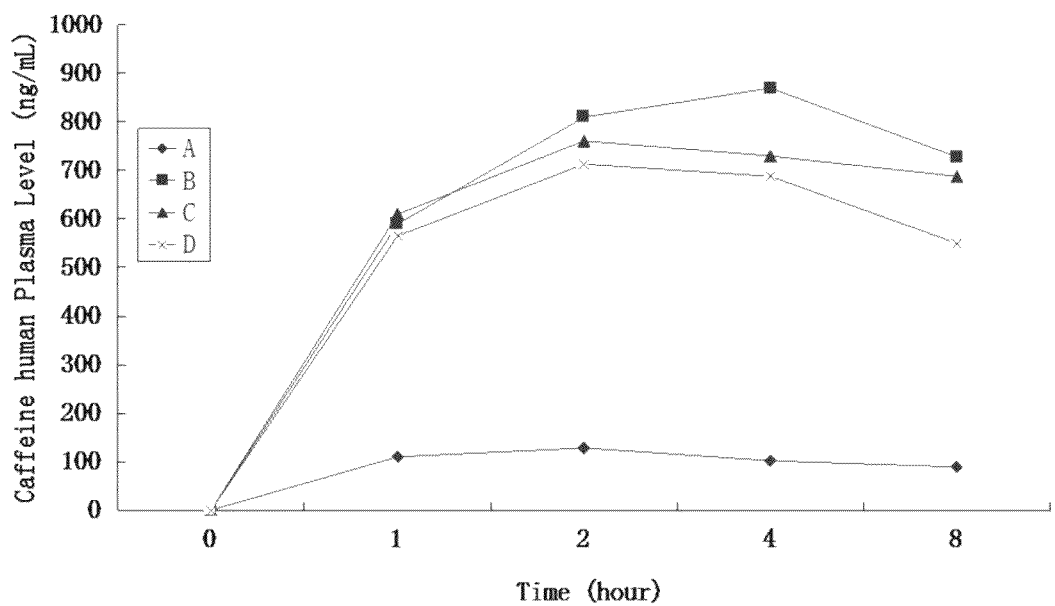

FIG. 5F shows effects of proline esters.HCl on transdermal delivery of caffeine in human. A: 1.05 ml of 2% caffeine in water was applied to skin on the neck of the body (20 cm×20 cm); B: 0.70 ml of 7% proline isopropyl ester.HCl and 3% caffeine in water was applied to skin on the back of the body (20 cm×20 cm); C: 0.70 ml of 7% proline methyl ester.HCl and 3% caffeine in water was applied to skin on the back of the body (20 cm×20 cm); D: 0.70 ml of 7% proline hexyl ester.HCl and 3% caffeine in water was applied to skin on the back of the body (20 cm×20 cm).

Figure 5G:
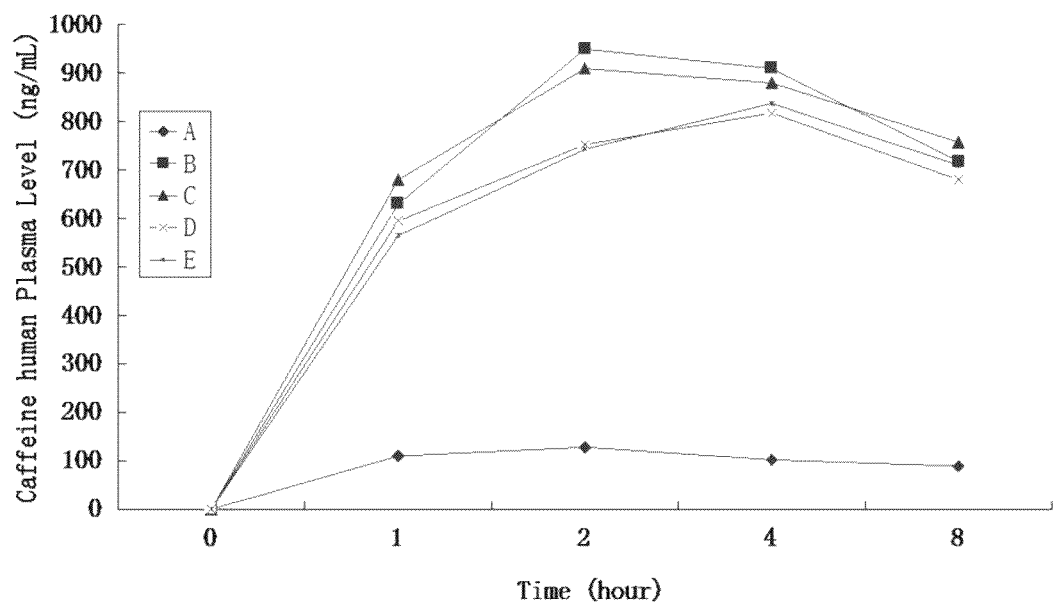

FIG. 5G shows effects of 2-(dialkylamino)alkyl 2-acetoxybenzoate hydrochloride on transdermal delivery of caffeine in human. A: 1.05 ml of 2% caffeine in water was applied to skin on the neck of the body (20 cm×20 cm); B: 0.35 ml of 7% 2-(Diethylamino)ethyl 2-acetoxybenzoate hydrochloride and 6% caffeine in water was applied to skin on the back of the body (20 cm×20 cm); C: 0.35 ml of 7% 2-(Diethylamino)propyl 2-acetoxybenzoate hydrochloride and 6% caffeine in water was applied to skin on the back of the body (20 cm×20 cm); D: 0.35 ml of 7% 2-(dimethylamino)hexyl 2-acetoxybenzoate hydrochloride and 6% caffeine in water was applied to skin on the back of the body (20 cm×20 cm); E: 0.35 ml of 7% 2-(dibutylamino)ethyl 2-acetoxybenzoate hydrochloride and 6% caffeine in water was applied to skin on the back of the body (20 cm×20 cm).

Figure 5H:
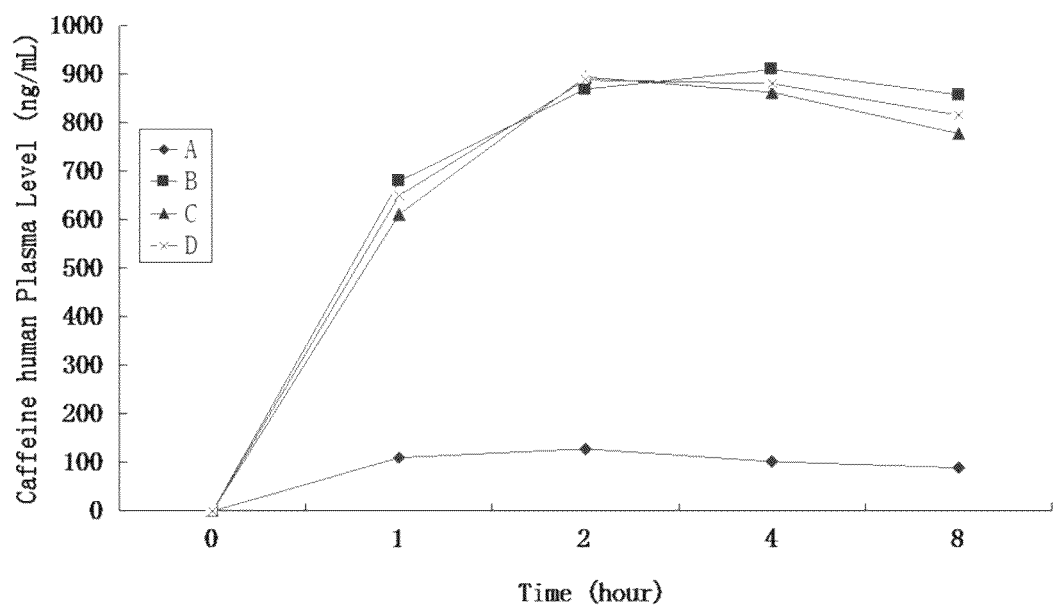

FIG. 5H shows effects of 2-(Dialkylamino)ethyl 2-(4-isobutylphenyl)propionate hydrochloride on transdermal delivery of caffeine in human. A: 1.05 ml of 2% caffeine in water was applied to skin on the neck of the body (20 cm×20 cm); B: 0.70 ml of 7% 2-(Diethylamino)pentyl 2-(4-isobutylphenyl)propionate hydrochloride and 3% caffeine in water was applied to skin on the back of the body (20 cm×20 cm); C: 0.70 ml of 7% 2-(Dimethylamino)ethyl 2-(4-isobutylphenyl)propionate hydrochloride and 3% caffeine in water was applied to skin on the back of the body (20 cm×20 cm); D: 0.70 ml of 7% 2-(Diethylamino)butyl 2-(4-isobutylphenyl) propionate hydrochloride and 3% caffeine in water was applied to skin on the back of the body (20 cm×20 cm).

FIG. 6 shows effects of various HA of tryptophan esters on transdermal delivery of caffeine in human. A: 1.05 ml of 2% caffeine in water was applied to skin on the neck of the body (20 cm×20 cm); B: 0.35 ml of 7% tryptophan isopropyl ester-.HCl and 6% caffeine in water was applied to skin on the back of the body (20 cm×20 cm); C: 0.35 ml of 7% tryptophan isopropyl ester.HF and 6% caffeine in water was applied to skin on the back of the body (20 cm×20 cm); D: 0.35 ml of 7% tryptophan isopropyl ester.HBr and 6% caffeine in water was applied to skin on the back of the body (20 cm×20 cm); E: 0.35 ml of 7% tryptophan isopropyl ester.Hl and 6% caffeine in water was applied to skin on the back of the body (20 cm×20 cm); F: 0.35 ml of 7% tryptophan isopropyl ester.citric acid and 6% caffeine in water was applied to skin on the back of the body (20 cm×20 cm); G: 0.35 ml of 7% tryptophan isopropyl ester.acetic acid and 6% caffeine in water was applied to skin on the back of the body (20 cm×20 cm), H: 0.35 ml of 7% tryptophan isopropyl ester.benzoic acid and 6% caffeine in water was applied to skin on the back of the body (20 cm×20 cm); I: 0.35 ml of 7% tryptophan isopropyl ester.lactic acid and 6% caffeine in water was applied to skin on the back of the body (20 cm×20 cm).

What is claimed is:

1. A composition comprising caffeine, a non-toxic acid salt of a helper ester comprising a lipophilic portion and a primary, secondary, or tertiary amine group.

2. The composition according to claim 1, wherein the non-toxic acid salt is selected from the group consisting of HF, HCl, HBr, Hl, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

3. The composition according to claim 1, wherein the non-toxic acid salts of esters of amino acids and other acids are selected from the group consisting of Structure 1, Structure 2, Structure 3, Structure 4, Structure 5, Structure 6, Structure 7, Structure 8, Structure 9, Structure 10, Structure 11, Structure 12, Structure 13, Structure 14, Structure 15, Structure 16, and Structure 17, as shown below, Structure 1

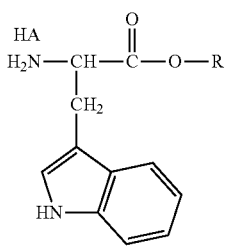

Structure 2

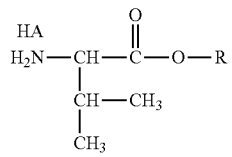

Structure 3

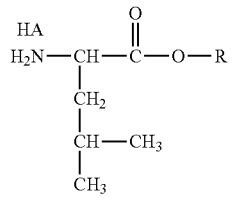

Structure 4

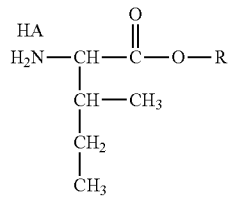

Structure 5

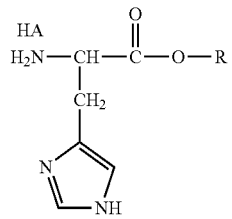

Structure 6

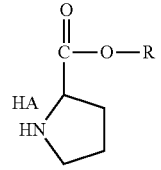

Structure 7

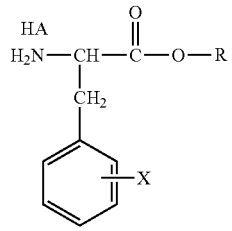

Structure 8

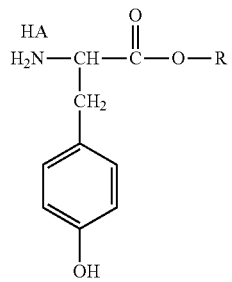

33
-continued

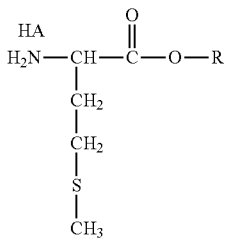

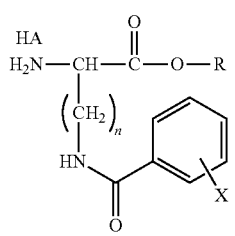

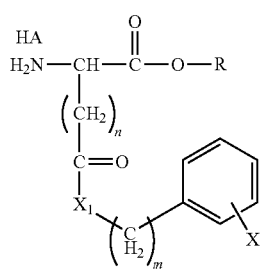

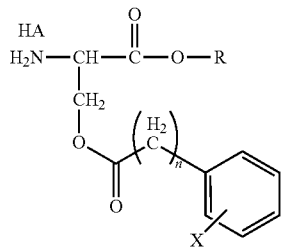

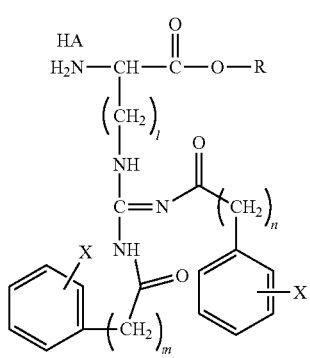

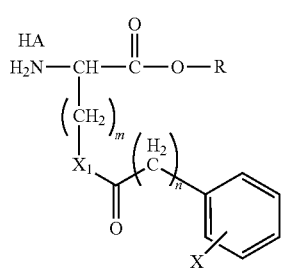

34
-continued

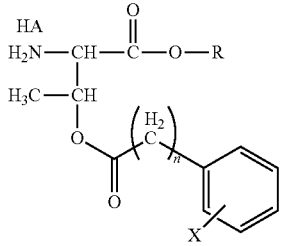

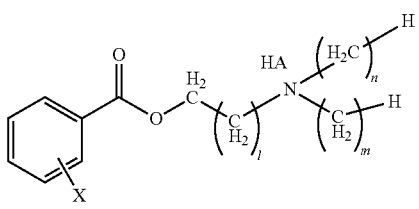

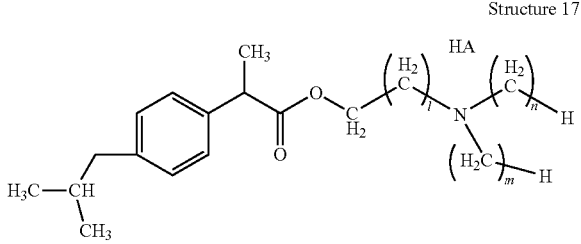

each X is independently selected from the group consisting of H, $NH_2$, $NHR_5$, OH, $OCOR_5$, Cl, Br, I, CN, $R_5COS$, $R_5O$, $R_5OCONH$, $CH_2NHR_8$, $R_5SO_2$, $R_5SO$, $NH_2SO_2$, and $NO_2$;

each $X_1$ is independently selected from the group consisting of O, S, $NH_2$, and $NHR_5$;

each $R_1$, $R_5$ and R is independently selected from the group consisting of H, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_1$, or any other pharmaceutically acceptable groups;

each HA is independently selected from the group consisting of HF, HCl, HBr, Hl, acetic acid, citric acid, benzoic acid, lactic acid, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, pamoic acid, and any other acid that is non-toxic to humans and animals; and each l, m, and n is independently selected from the group consisting of 0, 1, 2, 3, 4, 5, 6, 7, 8, 9, and 10.

4. The composition according to claim 1, wherein the helper ester is selected from the group consisting of L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, 2-(dialkylamino)ethyl 2-(4-isobutylphenyl)propionate hydrochloride, and 2-(dialkylamino)alkyl 2-acetoxybenzoate hydrochloride.

5. The composition according to claim 1, wherein the amount of caffeine present in the composition ranges from about 1 percent to about 20 percent, from about 2 percent to about 12 percent, from about 3 percent to about 10 percent, and from about 4 percent to about 7 percent of the composition by weight.

6. The composition according to claim 1, wherein the amount of the salt of helper ester ranges from about 1 percent to about 50 percent, from about 2 percent to about 25 percent, from about 3 percent to about 10 percent, and from about 4 percent to about 7 percent of the composition by weight.

7. The composition according to claim 1, further comprising an amino acid selected from the group consisting of L-tryptophan, L-leucine, L-isoleucine, L-proline, L-tyrosine, L-phenylalanine, L-arginine, L-alanine, L-asparagine, L-aspartic acid, L-cysteine, L-glutamine, L-histidine, L-lysine, L-methionine, L-serine, L-threonine, L-valine, D-tryptophan, D-leucine, D-isoleucine, D-proline, D-tyrosine, D-phenylalanine, D-arginine, D-alanine, D-asparagine, D-aspartic acid, D-cysteine, D-glutamine, D-histidine, D-lysine, D-methionine, D-serine, D-threonine, D-valine, and glycine; and the amount of the amino acid ranges from about 0.001 percent to about 50 percent, from about 0.01 percent to about 20 percent, from about 0.1 percent to about 10 percent, and from about 0.1 percent to about 2 percent of the composition by weight.

8. The composition according to claim 1, further comprising water, and the amount of water ranges from about 1 percent to about 99 percent, from about 50 percent to about 95 percent, from about 70 percent to about 90 percent, and from about 75 percent to about 88 percent of the composition by weight.

9. The composition according to claim 1, further comprising an alcohol selected from the group consisting of ethanol, propanol, isopropanol, and butanol; and the amount of the alcohol ranges from about 1 percent to about 99 percent, from about 5 percent to about 75 percent, from about 10 percent to about 50 percent, and from about 10 percent to about 25 percent of the composition by weight.

10. The composition according to claim 1, further comprising menthol, and the amount of menthol ranges from about 0.01 percent to about 20 percent, from about 0.1 percent to about 10 percent, from about 1 percent to about 5 percent, and from about 1 percent to about 3 percent of the composition by weight.

11. The composition according to claim 1, further comprising an additive selected from the group consisting of preservatives, wetting agents, emulsifying agents, dispersing agents, antibacterial agents, antifungal agents paraben, chlorobutanol, and phenol sorbic acid.

12. The composition according to claim 1, further comprising glycerin; and the amount of glycerin ranges from about 1 percent to about 50 percent, from about 1 percent to about 25 percent, from about 5 percent to about 20 percent, or from about 5 percent to about 10 percent of the compositions by weight.

13. The composition according to claim 1, further comprising dimethyl sulfoxide (DMSO); and the amount of DMSO ranges from about 1 percent to about 80 percent, from about 5 percent to about 70 percent, from about 10 percent to about 50 percent, or from about 20 percent to about 30 percent of the compositions by weight.

14. A method for delivery of caffeine to a subject comprising applying the composition according to claim 1 to the subject by a transdermal, transmucosal, trans-nasal or topical method.

15. The method according to claim 14, wherein the composition is applied to the subject by a spray method.

16. The method according to claim 14, wherein the composition is applied to the subject by a roll-on method.

17. A kit comprising the composition according to claim 1 and a spray bottle.

18. A kit comprising the composition according to claim 1 and a roll-on bottle.

19. A kit comprising the composition according to claim 1 and a cotton swab.

* * * * *